(12) United States Patent
Chu et al.

(10) Patent No.: US 6,689,374 B2
(45) Date of Patent: Feb. 10, 2004

(54) BIODEGRADABLE AND/OR BIOABSORBABLE FIBROUS ARTICLES AND METHODS FOR USING THE ARTICLES FOR MEDICAL APPLICATIONS

(75) Inventors: Benjamin Chu, Setauket, NY (US); Benjamin S. Hsiao, Setauket, NY (US); Dufei Fang, Painted Post, NY (US); Collin Brathwaite, Setauket, NY (US)

(73) Assignee: The Research Foundation of State University of New York, Stony Brook, NY (US)

( * ) Notice: Subject to any disclaimer, the term of this patent is extended or adjusted under 35 U.S.C. 154(b) by 0 days.

(21) Appl. No.: 10/375,329

(22) Filed: Feb. 27, 2003

(65) Prior Publication Data

US 2003/0228350 A1 Dec. 11, 2003

Related U.S. Application Data

(62) Division of application No. 09/859,007, filed on May 16, 2001.

(51) Int. Cl.⁷ .................................................. A61F 2/02
(52) U.S. Cl. ........................ 424/423; 424/424; 424/425; 424/426
(58) Field of Search ................................ 424/423, 424, 424/425, 426

(56) References Cited

U.S. PATENT DOCUMENTS

| 3,975,565 A | 8/1976 | Kendall |
| 4,043,331 A | 8/1977 | Martin et al. |
| 4,323,525 A | 4/1982 | Bornat |
| 4,345,414 A | 8/1982 | Bornat et al. |
| 4,468,922 A | 9/1984 | McCrady et al. |
| 4,689,186 A | 8/1987 | Bornat |
| 4,810,180 A | 3/1989 | Isner |
| 4,840,626 A | 6/1989 | Linsky et al. |
| 4,878,908 A | 11/1989 | Martin et al. |
| 4,911,867 A | 3/1990 | Burlet et al. |
| 5,066,755 A | 11/1991 | Lemstra |
| 5,296,172 A | 3/1994 | Davis et al. |
| 5,480,436 A | 1/1996 | Bakker et al. |
| 5,508,036 A | 4/1996 | Bakker et al. |
| 5,569,528 A | 10/1996 | Van der Loo et al. |
| 5,714,159 A | 2/1998 | Shalaby |
| 5,783,111 A | 7/1998 | Ikkala et al. |
| 5,795,584 A | 8/1998 | Totakura et al. |

(List continued on next page.)

FOREIGN PATENT DOCUMENTS

| WO | WO98/03267 | 1/1998 |
| WO | WO01/26610 A1 | 4/2001 |
| WO | WO01/27365 A1 | 4/2001 |

OTHER PUBLICATIONS

Dzenis et al, "Polymer Hybrid Nano/Micro Composites," Proceedings of the American Society for Composites = Ninth technical Conference, pp. 657–665.*

(List continued on next page.)

Primary Examiner—Carlos Azpuru
(74) Attorney, Agent, or Firm—Hoffmann & Baron, LLP

(57) ABSTRACT

Biodegradable and/or bioabsorable fibrous articles and methods for using the articles in medical applications are disclosed. The biodegradable and/or bioabsorable fibrous articles, which are formed by elctrospinning fibers of biodegradable and/or bioabsorbable fiberizable material, comprise a composite (or asymmetric composite) of different biodegradable and/or bioabsorbable fibers. Articles having specific medical uses include an adhesion-reducing barrier and a controlled delivery system. The methods include methods for reducing surgical adhesions, controlled delivery of a medicinal agent and providing controlled tissue healing.

29 Claims, 13 Drawing Sheets

U.S. PATENT DOCUMENTS

| | | |
|---|---|---|
| 6,010,692 A | 1/2000 | Goldberg et al. |
| 6,013,371 A | 1/2000 | Hager et al. |
| 6,037,331 A | 3/2000 | Shalaby et al. |
| 6,056,970 A | 5/2000 | Greenawalt et al. |
| 6,060,582 A | 5/2000 | Hubbell et al. |
| 6,090,910 A | 7/2000 | Shinoda et al. |
| 6,106,913 A | 8/2000 | Scardino et al. |
| 6,218,441 B1 | 4/2001 | Meluch et al. |

OTHER PUBLICATIONS

Dzenis et al., "Polymer Hybrid Nano/Micro Composites," *Proceedings of the American Society for Composites–Ninth Technical Conference*, pp. 657–65 (1994).

Bezwada et al., "Poly(p–Dioxanone) and Its Copolymers," *Handbook of Biodegradable Polymers*, # 29–61 (1997).

* cited by examiner

Spun membrane without salt

Spun membrane with 1 wt% KH$_2$PO$_4$

Biodegradation rate of electrospun membr

SEM image of electrospun PLAmembrane

FIG-12 Membrane after 1 week of degradation
FIG-11 Duel thickness PLA membrane

BIODEGRADABLE AND/OR BIOABSORBABLE FIBROUS ARTICLES AND METHODS FOR USING THE ARTICLES FOR MEDICAL APPLICATIONS

This application is a Divisional of Ser. No. 09/859,007 filed on May 16, 2001.

BACKGROUND OF INVENTION

The present invention relates to biodegradable and/or bioabsorbable fibrous articles. More specifically, the present invention is directed to products and methods having utility in medical applications. In one embodiment, the fibrous articles of the invention are polymeric membranes.

Polymeric membranes produced by an electrospinning technique have been suggested as being useful for biological membranes such as substrates for immobilized enzymes and catalyst systems, wound dressing materials and artificial blood vessels, as well as for aerosol filters and ballistic garments.

Electrospinning is an atomization process of a conducting fluid which exploits the interactions between an electrostatic field and the conducting fluid. When an external electrostatic field is applied to a conducting fluid (e.g., a semi-dilute polymer solution or a polymer melt), a suspended conical droplet is formed, whereby the surface tension of the droplet is in equilibrium with the electric field. Electrostatic atomization occurs when the electrostatic field is strong enough to overcome the surface tension of the liquid. The liquid droplet then becomes unstable and a tiny jet is ejected from the surface of the droplet. As it reaches a grounded target, the material can be collected as an interconnected web containing relatively fine, i.e. small diameter, fibers. The resulting films (or membranes) from these small diameter fibers have very large surface area to volume ratios and small pore sizes. However, no practical industrial process has been implemented for producing membranes useful for medical applications. This is because with the production of small fibers, such as nanosize fibers, the total yield of the process is very low and a scale-up process, which maintains the performance characteristics of the films (or membranes), cannot be easily achieved.

U.S. Pat. No. 4,323,525 is directed to a process for the production of tubular products by electrostatically spinning a liquid containing a fiber-forming material. The process involves introducing the liquid into an electric field through a nozzle, under conditions to produce fibers of the fiber-forming material, which tend to be drawn to a charged collector, and collecting the fibers on a charged tubular collector which rotates about its longitudinal axis, to form the fiberous tubular product. It is also disclosed that several nozzles can be used to increase the rate of fiber production. However, there is no suggestion or teaching of how to control the physical characteristics of the tubular product, other than by controlling the charge and rotation speed of the tubular collector. It is further noted that the spinning process of the '525 patent is used to fabricate tubular products having a homogenous fiber matrix across the wall thickness.

U.S. Pat. No. 4,689,186 is directed to a process for the production of polyurethane tubular products by electrostatically spinning a fiber-forming liquid containing the polyurethane. It is disclosed that auxiliary electrodes can be placed around the collector to help facilitate collection of the fibers. It is disclosed that the auxiliary electrodes can be arranged to facilitate separation or to prevent adhesion of the formed fibers. There is no teaching or suggestion of independently controlling jet formation, jet acceleration and fiber collection. It is also noted that the spinning process of the '186 patent is used to fabricate tubular products having a homogenous fiber matrix across the wall thickness.

In one aspect, the present invention is directed to products and methods for preventing the formation of post-surgical adhesions between a healing trauma site and adjacent surrounding tissue.

Adhesion formation is a natural and inevitable consequence of surgery. Injury, surgical incisions, abrasion or other operative damage to the peritoneum, pleural or abdominal cavity results in an outpouring of a serosanguinous exudate. This exudate can accumulate on the injured surface and subsequently coagulate, producing fibrinous bands between abutting surfaces which can become organized by fibroblast proliferation to become collagenous adhesions. Adhesions are also known to form at bone fracture sites resulting in adhesions between the bone fracture surface and the surrounding tissue.

Adhesions can lead to serious complications. For example, adhesions that form in relation to intestinal surgery such as bowel resection, hernia repair, etc., may cause obstruction of the intestine. Adhesions that form near a bone fracture site may reduce or hinder the normal movement of the area of repair by restricting the natural movement of tendons over the adjacent bone. Adhesions may also form in the vicinity of nerves and disrupt nerve transmissions with a resultant diminution of sensory or motor function. Adhesions have also been known to lead to female infertility, chronic debilitating pain and difficulty with future operations. Typically, a patient will often have to undergo additional surgery to remove adhesions, only to have them reform.

Various methods and substances have been used in the hope of preventing post-operative adhesions. Certain drugs and surfactants have been suggested. For example, U.S. Pat. No. 4,911,926 is directed to adhesion prevention by application of aqueous and non-aqueous compositions of a polyoxyalkylene block copolymer to injured areas of the peritoneal or pleural cavity or organs situated therein subsequent to surgical injury.

Other surgical adjuvants have been used in an attempt to minimize or prevent adhesions following surgery, including anti-inflammatory drugs (such as corticosteroids) to decrease vascular permeability, antihistamines to reduce fibroblast proliferation, anticoagulants (such as heparin) and antibiotics (such as vibramycin or metokin) to reduce the incidence of infection. However, the use of drugs or compositions which are applied to the surgical area have only had limited success in preventing adhesions.

Another approach to adhesion prevention involves application of a physical barrier at the area of surgical injury. The theory is that a mechanical barrier, placed between the injured, healing serosal surfaces, which persists until all serosal healing has taken place will prevent adhesions and the sequela, e.g., small bowel obstruction. Bioabsorbable materials in the form of barrier layers to prevent adhesions of tissues which have been suggested include products based on cellulose materials. However, the use of commercial cellulose based products to prevent adhesions has certain drawbacks. For example, the performance in preventing adhesions is limited. Furthermore, certain products have been reported to have handling problems during surgery or can cause scars after use.

U.S. Pat. No. 4,674,488 is directed to interposing a barrier layer of soft biological tissue, such as collagen, collagen-fabric films, collagen membranes, or reconstituted collagen or Dacron™, mesh, at the interface of a bone fracture and the surrounding tissue. U.S. Pat. No. 4,603,695 is directed to a molded polymeric material for preventing adhesion of vital tissues. The polymeric material is made of a biodegradable and absorbable polymer such as certain polyesters, collagen, amino acid polymers and chitin and may be placed where there is a possibility of adhesion setting in. Although biological materials, such as collagen, are generally "biocompatible," they can generate scars when implanted in certain forms, and it is difficult to precisely control the degradation of such materials.

Other materials have also been used to form physical barriers in an attempt to prevent adhesions, including silicone elastomers, gelatin films and knit fabrics of oxidized regenerated cellulose (hereinafter ORC). In some cases, it is suggested that heparin, heparinoid, or hexuronyl hexosaminogly can be incorporated into the matrix of an ORC fabric or other matrices of hyaluronic acid, cross-linked and uncross-linked collagen webs, synthetic resorbable polymers, gelatin films, absorbable gel films, oxidized cellulose fabrics and films which are fabricated into a form that is said to be drapable, conformable and adherent to body organs and substantially absorbable within 30 days. See, e.g., U.S. Pat. No. 4,840,626 or EPA Publication No. 0 262 890 or EPA Publication No. 0 372 969. However, as discussed above, it is difficult to precisely control the degradation rate of many of these materials and scar tissue can result from use of many of the materials.

Physical barriers are also used to cover and protect wound sites. PCT/US91/08972 is directed to a surgical article having a bioabsorbable fibrous matrix in a laminar relationship with a bioabsorbable cell barrier sheet. U.S. Pat. No. 5,092,884 and EPA Publication No. 0 334 046 are directed to a surgical composite structure having absorbable and non-absorbable components which may be useful for repairing anatomical defects, e.g., preventing hernia formation in an infected area. The nonabsorbable portion of the composite acts as a reinforcement material. The growth of natural tissue is said to be enhanced by controlled degradation of the absorbable portion. U.S. Pat. No. 5,035,893 relates to a wound covering composition having a sheet of biopolymeric material and a film of polyurethane resin. An antibacterial agent may be provided between the polyurethane film and the sheet of biopolymeric material, thereby forming a three-layer wound covering material. With the cure of the wound, it is said that the biopolymeric material is taken in as living tissue and the polyurethane film can be peeled off from the sheet without hurting the surface of a wound. Again, the use of many biopolymeric materials can result in the formation of scar tissue.

Thus, there is a need for improved membranes and other fibrous articles, which can be produced on an industrial scale, and for improved products and methods for reducing the formation of post-surgical adhesions, as well as for other medical applications, which do not have the above-mentioned disadvantages.

SUMMARY OF INVENTION

According to the present invention, it has now been found that biodegradable and/or bioabsorbable articles, e.g. membranes, having improved performance and handling characteristics for medical applications can be provided without the above-mentioned disadvantages.

In one aspect, the invention relates to a biodegradable and/or bioabsorbable fibrous article formed by electrospinning fibers of biodegradable and/or bioabsorbable fiberizable material, in which the article contains a composite of different biodegradable and/or bioabsorbable fibers.

In another aspect, the invention relates to a biodegradable and/or bioabsorbable fibrous article formed by electrospinning fibers of biodegradable and/or bioabsorbable fiberizable material, in which the article contains an asymmetric composite of different biodegradable and/or bioabsorbable fibers.

Different fibers can include fibers of different diameters, fibers of different biodegradable and/or bioabsorbable materials, or fibers of both different diameters and different biodegradable and/or bioabsorbable materials.

Preferably, the article will contain at least about 20 weight percent of submicron diameter fibers, more preferably, the article will contain at least about 50 weight percent of submicron diameter fibers.

Preferably, the biodegradable and/or bioabsorbable fiberizable material is a biodegradable and/or bioabsorbable polymer. The biodegradable and/or bioabsorbable polymer preferably contains a monomer selected from the group consisting of a glycolide, lactide, dioxanone, caprolactone, trimethylene carbonate, ethylene glycol and lysine.

In one embodiment the biodegradable and/or bioabsorbable polymer contains a biodegradable and/or bioabsorbable linear aliphatic polyester, more preferably a polyglycolide or a poly(glycolide-co-lactide) copolymer.

In another embodiment the biodegradable and/or bioabsorbable fiberizable material contains a material derived from biological tissue, e.g., collagen, gelatin, polypeptides, proteins, hyaluronan acid and derivatives or synthetic biopolymers.

The fibers of different biodegradable and/or bioabsorbable materials can include fibers having different chemical composition, such as different polymeric materials, different molecular weights of the same polymeric material, different blends of polymers, materials having different additives or materials having different concentration of additives.

In another embodiment the article will contain different fibers, i.e. different diameters and/or different materials, having diameters in the range from a few nanometers up to almost about one micron, more preferably about 10 up to about 1000 nanometers and most preferably from about 20 to about 500 nanometers. The fibers of different diameters can include both fibers having diameters less than 300 nanometers and fibers having diameters greater than 300 nanometers.

The article can also contain small blobs of biodegradable and/or bioabsorbable material. Preferably, the small blobs will have diameters in the range of about 20 to about 500 nanometers and, more preferably, about 200 to about 1500 nanometers.

In one embodiment, the article also contains at least one medicinal agent. The medicinal agent can be contained within the biodegradable and/or bioabsorbable material itself, including within the fibers or within the small blobs of material, if present. In such a case, the fibers (and/or small blobs) can contain different concentrations of the medicinal agent or different medicinal agents.

The article can also have the structure of a plurality of layers, wherein at least one of the layers is a composite (or asymmetric composite) of different biodegradable and/or bioabsorbable fibers. In such a case, the article can also contain at least one medicinal agent between at least two of the layers.

In one embodiment, the above described fibrous articles are in the form of a membrane.

The membrane according to the invention will preferably have a thickness in the range of about 10 to about 5000 microns, more preferably about 20 to about 1000 microns.

In another aspect, the invention relates to a fibrous article formed by electrospinning different fibers of different materials, in which the article contains a composite of different fibers containing fibers of at least one biodegradable material and fibers of at least one non-biodegradable material. Preferably, the compositite of different fibers will contain submicron diameter fibers. The composite can be an asymmetric composite.

In another aspect, the invention is directed towards an adhesion-reducing barrier containing a biodegradable and/or bioabsorbable membrane, in which the membrane contains:

a composite of different biodegradable and/or bioabsorbable fibers; or an asymmetric composite of different biodegradable and/or bioabsorbable fibers.

Preferably, the adhesion-reducing barrier contains the above described membranes.

In yet another aspect, the invention is directed to a method for reducing surgical adhesions which involves positioning an adhesion-reducing barrier between the site of surgical activity and neighboring tissues. The barrier contains a biodegradable and/or bioabsorbable membrane, in which the membrane contains:

a composite (or an asymmetric composite) of different biodegradable and/or bioabsorbable fibers;

a plurality of layers, with at least two layers having different biodegradable and/or bioabsorbable fibers from each other; or sub-micron diameter biodegradable and/or bioabsorbable fibers, having at least one medicinal agent contained within the fibers.

Preferably, the method involves use of the above described barriers.

In yet another aspect, the invention is directed to a system for controlled delivery of a medicinal agent which contains the medicinal agent to be delivered and a biodegradable and/or bioabsorbable fibrous article physically associated with the medicinal agent to release the agent at a controlled rate. The article contains a composite of different biodegradable and/or bioabsorbable fibers or an asymmetric composite of different biodegradable and/or bioabsorbable fibers.

Preferably, the system will include the articles and biodegradable and/or bioabsorbable materials discussed above.

In another aspect, the invention is directed to a method for the controlled delivery of a medicinal agent which involves implanting at a target site in an animal, a system for controlled delivery of a medicinal agent. The system for controlled delivery of a medicinal agent contains the medicinal agent to be delivered and a biodegradable and/or bioabsorbable fibrous article physically associated with the medicinal agent to release the agent at a controlled rate. The article contains a composite of different biodegradable and/or bioabsorbable fibers or an asymmetric composite of different biodegradable and/or bioabsorbable fibers.

Preferably, the method involves use of the above described system.

The present invention provides biodegradable and/or bioabsorbable fibrous articles, e.g. membranes, having improved performance and handling characteristics for medical applications, including improved performance in preventing adhesions. The invention also provides fibrous articles containing fibers of controlled size and having controlled morphology and biodegradation rate with utility in a controlled delivery system.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE FIGURES

FIG. 11 is an SEM of the PLA membrane described in Example 7.

FIG. 12 is an SEM of the PLA membrane described in Example 7 after 1 week of degradation.

DETAILED DESCRIPTION OF THE INVENTION

Figure 1:
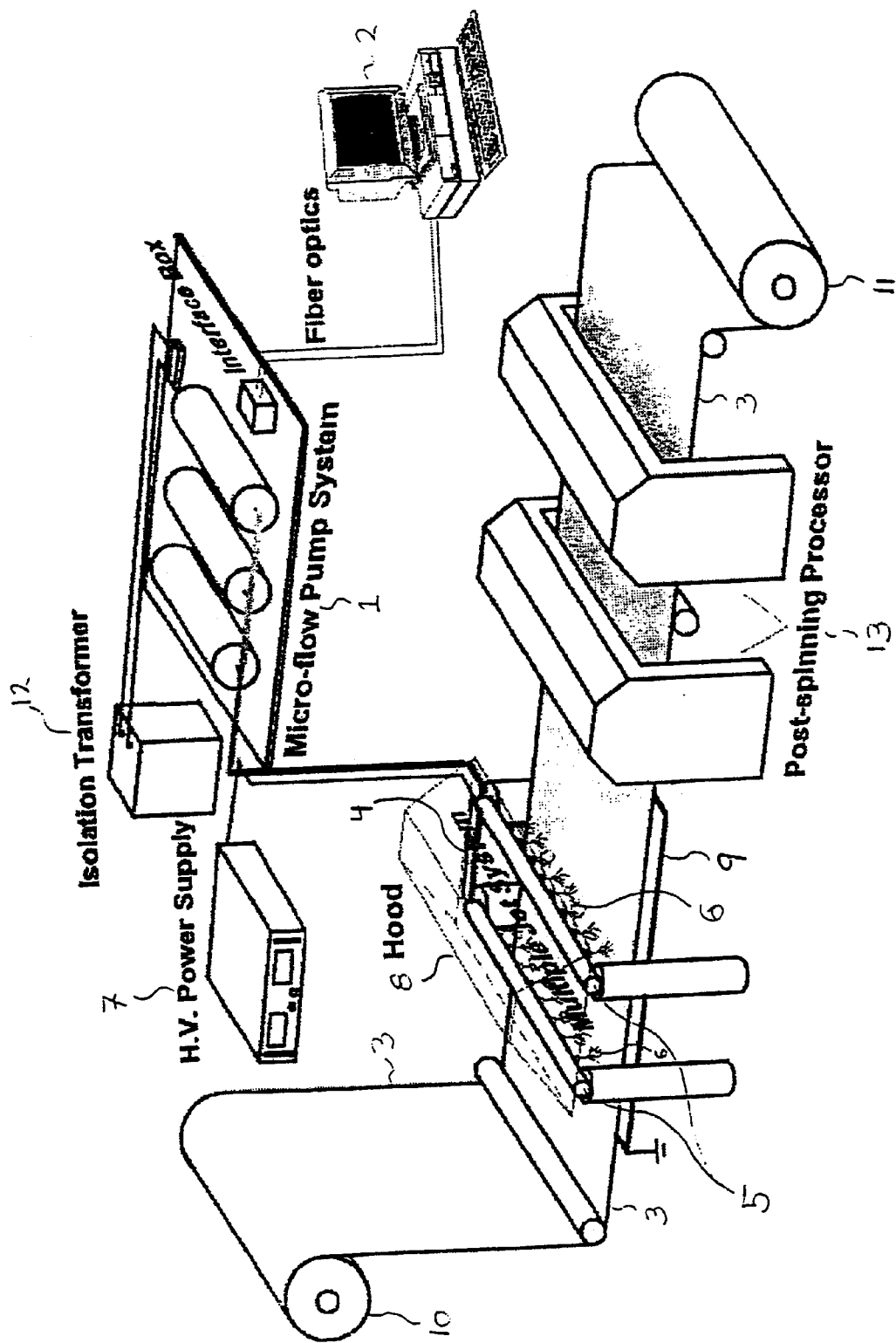
FIG. 1 is a schematic of an electrospinning system.

The present invention is directed to biodegradable and/or bioabsorbable fibrous articles and methods for using the articles for medical applications including reducing the formation of post-surgical adhesions between a healing trauma site and the adjacent tissue and controlled delivery systems.

In one aspect, the invention relates to a biodegradable and bioabsorbable fibrous article formed by electrospinning fibers of biodegradable and/or bioabsorbable fiberizable material in which the article contains a composite of different biodegradable and/or bioabsorbable fibers.

In another aspect, the article can contain an asymmetric composite of different biodegradable and/or bioabsorbable fibers.

In yet another aspect, the article can also include fibers of at least one non-biodegradable/non-bioabsorbable material.

By the term biodegradable is intended a material which is broken down (usually gradually) by the body of an animal, e.g. a mammal, after implantation.

By the term bioabsorbable is intended a material which is absorbed or resorbed by the body of an animal, e.g. a mammal, after implantation, such that the material eventually becomes essentially non-detectable at the site of implantation.

By the terminology "biodegradable and/or bioabsorbable fiberizable material" is intended any material which is biocompatible, as well as biodegradable and/or bioabsorbable, and capable of being formed into fibers, as described more fully below. The material is also capable of being formed into a fibrous article which is suitable for implantation into an animal and capable of being biodegraded and/or bioabsorbed by the animal.

The biodegradable and/or bioabsorbable fiberizable material is preferably a biodegradable and bioabsorbable polymer. Examples of suitable polymers can be found in Bezwada, Rao S. et al. (1997) *Poly(p-Dioxanone) and its copolymers, in Handbook of Biodegradable Polymers*, A. J. Domb, J. Kost and D. M. Wiseman, editors, Hardwood Academic Publishers, The Netherlands, pp. 29–61, the disclosure of which is incorporated herein by reference in its entirety.

In a preferred embodiment the biodegradable and/or bioabsorbable polymer contains a monomer selected from the group consisting of a glycolide, lactide, dioxanone, caprolactone, trimethylene carbonate, ethylene glycol and lysine. By the terminology "contains a monomer" is intended a polymer which is produced from the specified monomer(s) or contains the specified monomeric unit(s). The polymer can be a homopolymer, random or block co-polymer or hetero-polymer containing any combination of these monomers. The material can be a random copolymer, block copolymer or blend of homopolymers, copolymers, and/or heteropolymers that contains these monomers.

In one embodiment, the biodegradable and/or bioabsorbable polymer contains bioabsorbable and biodegradable linear aliphatic polyesters such as polyglycolide (PGA) and its random copolymer poly(glycolide-co-lactide) (PGA-co-PLA). The FDA has approved these polymers for use in surgical applications, including medical sutures. An advantage of these synthetic absorbable materials is their degradability by simple hydrolysis of the ester backbone in aqueous environments, such as body fluids. The degradation products are ultimately metabolized to carbon dioxide and water or can be excreted via the kidney. These polymers are very different from cellulose based materials, which cannot be absorbed by the body.

These materials are also effective drug carriers for pharmaceutical products, as they meet several drug release criteria including a biocompatible and biodegradable polymer matrix that provides efficient drug loading. The degradation rate of these materials, as well as the release rate of entrapped drugs, can only be roughly controlled by varying the molecular structure and the molecular weight as there is no linear relationship between the physical properties of the constituent homopolymers or their copolymers. However, by controlling the filament diameter (to nanometer sizes) and the assembly morphology as described more fully below, the degradation rate and the drug release rate can be finely tuned. For example, Dunne et al. examined the influence of processing conditions, particle characteristics and media temperature on the degradation of PGA-co-PLA spherical particles. They found that a linear relationship between the degradation rate and particle size existed, with the larger particles degrading fastest.

Other examples of suitable biocompatible polymers are polyhydroxyalkyl methacrylates including ethylmethacrylate, and hydrogels such as polyvinylpyrrolidone, polyacrylamides, etc. Other suitable bioabsorbable materials are biopolymers which include collagen, gelatin, alginic acid, chitin, chitosan, fibrin, hyaluronic acid, dextran, polyamino acids, polylysine and copolymers of these materials. Any combination, copolymer, polymer or blend thereof of the above examples is contemplated for use according to the present invention. Such bioabsorbable materials may be prepared by known methods.

Particularly useful biodegradable and/or bioabsorbable polymers include poly-lactides, poly-glycolides, polycarprolactone, polydioxane and their random and block copolymers. Examples of specific polymers include poly D,L-lactide, polylactide-co-glycolide (85:15) and polylactide-co-glycolide (75:25).

Preferably, the biodegradable and/or bioabsorbable polymers used in the articles of the present invention will have a molecular weight in the range of about 1,000 to about 8,000,000 g/mole, more preferably about 4,000 to about 250,000 g/mole.

By the terminology "composite of different biodegradable and/or bioabsorbable fibers" is intended any combination of the different fibers interleaved with each other in the form of a fibrous matrix, which can be in the form of a membrane or other three dimensional form of tailored geometry, such as a tube, rod or plug.

By the terminology "asymmetric composite of different biodegradable and/or bioabsorbable fibers" is intended a composite of different biodegradable and/or bioabsorbable fibers, having at least one of non-homogeneous porosity or assembled morphology, variations in the ratio of different fibers, progressing through different regions of the composite material. For example, with reference to a membrane containing an asymmetric composite of different biodegradable and/or bioabsorbable fibers, the porosity, morphology or variations in fibers can be varied either in a direction perpendicular to or parallel with the surface of the membrane. Thus, an asymmetric composite of different biodegradable and/or bioabsorbable fibers can have 100 percent submicron diameter fibers on a first side of the membrane, zero percent submicron diameter fibers on the opposite side, and a progressively lower percentage of submicron diameter fibers in the direction from the first side across the thickness of the membrane.

By the terminology "different biodegradable and/or bioabsorbable fibers" is intended to include fibers of different diameters, fibers of different biodegradable and/or bioabsorbable materials, or fibers of both different diameters and different biodegradable and/or bioabsorbable materials.

By the terminology "fibers of different diameters" is intended that the article will include fibers having at least two different target (or intended) diameters.

By the terminology "fibers of different biodegradable and/or bioabsorbable materials" is intended to include fibers having different chemical composition, in the form of, for example, different polymeric materials, different molecular weights of the same polymeric material, or different additives (or concentration of additives), such as medicinal agents.

In one embodiment, the article will contain different fibers having diameters in the range from a few up to about 1,000 nanometers, more preferably about 10 up to about 1000 nanometers and most preferably about 20 to about 500 nanometers.

The article can contain fibers having different diameters with a controlled percentage of sub-micron diameter fibers. Preferably, the article will contain at least about 10 wt % of sub-micron diameter fibers, more preferably at least about 20 wt %, and most preferably at least about 50 wt %.

Optionally, the fibrous article can contain at least one medicinal agent. In such a case, one or more medicinal agents may be incorporated into the fibers of the article. Preferably, the medicinal agent(s) will be mixed with the bioabsorable material, e.g., polymer, prior to formation of the fibers.

In loading the medicinal agent, the medicine may need to be dissolved in a solvent that may not be compatible with the solvent used in the electrospinning process. A block copolymer, acting as a surfactant, can then be used to circumvent this difficulty. One block that forms the micellar shell is a polymer that is compatible with the fibrous material that will be used to form the nano-fibers and the other block that has a different chemical composition is more compatible with the medicinal agent. For example, a block copolymer of PLA-co-PEO could form a micelle that is compatible with the PLA solution while the inner PEO core that is more hydrophilic can be used to load more hydrophilic medicinal agents. The micellar property and uptake capacity can be determined by the chemical composition of the blocks, the molecular architecture, the block length, and the chain length ratio of the blocks. The micelles, being compatible with the fibrous material can be incorporated into the nano-fibers during processing. Furthermore, the drug release rate can also be controlled by the micellar property. For example, a glassy core can reduce the drug release rate.

By the term "medicinal agent" is intended any substance or mixture of substances which may have any clinical use in medicine. Thus medicinal agents include drugs, enzymes, proteins, peptides, glycoproteins, hormones or diagnostic agents such as releasable dyes or tracers which may have no biological activity per se, but are useful for diagnostic testing, e.g., MRI.

Examples of classes of medicinal agents that can be used in accordance with the present invention include antimicrobials, analgesics, antipyretics, anesthetics, antiepileptics, antihistamines, anti-inflammatories, cardiovascular drugs, diagnostic agents, sympathomimetic, cholinomimetic, antimuscarinics, antispasmodics, hormones, growth factors, muscle relaxants, adrenergic neuron blockers, anti-neoplastics, immunosuppressants, gastrointestinal drugs, diuretics, steroids and enzymes. It is also intended that combinations of medicinals can be used in accordance with the present invention.

Thus, in one embodiment of the present invention focal delivery and application of a medicinal agent to the wound site is achieved. Focal application can be more desirable than general systemic application in some cases, e.g., chemotherapy for localized tumors, because it produces fewer side effects in distant tissues or organs and also concentrates therapy at intended sites. Focal application of growth factors, anti-inflammatory agents, immune system suppressants and/or antimicrobials by the membranes of the present invention is an ideal drug delivery system to speed healing of a wound or incision. Focal application of anesthetics by the articles of the present invention is an ideal drug delivery system for pain management.

In one embodiment, the above described fibrous articles are in the form of a membrane. Although the discussion that follows is directed to membranes in accordance with the invention, it should be understood that the discussion is applicable to other three dimensional articles, including, but not limited to tubes, rods, plugs, blocks, etc.

In one aspect the invention is directed to biodegradable and/or bioabsorbable membranes having a controlled biodegradation rate. The chemical composition, i.e., specific polymers or blends of polymers, the fiber diameter, the membrane morphology, the molecular weight distribution and the porosity of the membrane can be used to control the degradation and/or absorption time for the membrane. As such, the membranes containing medicinal agents within the fibers themselves are well suited as a controlled drug delivery device, since the above-mentioned factors can also be used to control the rate of release of the medicinal agent.

The membrane can also contain a plurality of fibers which have different medicinal agents or different concentrations of medicinal agents. Such membranes offer unique treatment options with combinations of medicinal agents and release profiles.

In one embodiment, the membrane can contain a plurality of biodegradable and/or bioabsorbable non-woven layers. The layers can have the same or different chemical composition, fiber diameters, membrane morphology and porosity as discussed more fully above. Multiple layered membranes can offer yet another way to precisely control degradation and drug release rate.

In such an embodiment, it is also contemplated that medicinal agents can be incorporated between the layers of the multi-layered membrane, instead of or in addition to, incorporating the agents into the fiber structure itself.

In one embodiment, the membrane can be attached to a non-absorbable reinforcement layer, such as a Marlox mesh.

In another aspect, the invention relates to a fibrous article formed by elecrospinning different fibers of different materials, in which the article contains a composite of different fibers containing fibers of at least one biodegradable material and fibers of at least one non-biodegradable material.

In addition to drug delivery devices, the membranes of the present invention are particularly well suited for use as an adhesion-reducing barrier.

The membranes of the present invention may be employed as barriers between tissues or barriers between tissue and bone to prevent binding of tissue to tissue or of tissue to bone. Examples of uses of the devices of the present invention include, but are not limited to, barriers between the internal female reproductive organs (e.g., uterus, fallopian tubes, ovaries); barriers between the internal female reproductive organs and the peritoneum; barriers for use during laparoscopy; barriers between periodontal tissue; barriers between cartilage or between cartilage and bone; barriers between digestive organs; spinal barriers; barriers between digestive organs and peritoneum; barriers between the epicardium and surrounding structures such as the pericardium, mediastinal fat, pleura, and sternum; barriers between tendons and tendon sheaths, such as those in the wrist and ankle; bone fracture wraps; barriers between muscle tissue and bone; barriers between the esophagus and mediasternum; barriers between the gall bladder or pancreas and the peritoneum; and barriers for scrotal surgery.

The membranes of the present invention may also be used for guided tissue regeneration. For example, the membranes may be used to cover internal perforations, such as, for example, perforations in blood vessels, internal organs, the nasal septum, and the eardrum membrane, and may be used to reconstruct the abdominal wall, or to reinforce areas prone to or showing scar formation, such as, for example, inguinal hernias. The membrane therefore acts as a patch for covering the perforation until complete healing, followed by copolymer absorption, is achieved. It is also contemplated that the membranes may be employed as a cover for burns, whereby the device acts as a patch until the burn is healed.

The membranes of the present invention may be employed as a scaffolding to treat ulcers. A porous membrane can be designed to stimulate the proliferation of fibrous tissue, as a consequence of which, for example, in the case of ulcers, the wound bed becomes more optimal for the regeneration of skin.

The membranes of the present invention may also be employed in redirect healing, whereby the devices are employed to protect nerves and organ coverings, and mucosa during the healing process, whereby the formation of fibrous tissue over such nerves, organs, and mucosa is prevented.

The membranes may also be employed to prevent the formation of internal blood clots after surgery or traumatic injury.

The membranes may also be employed in covering denuded epithelial surfaces or weakened areas such as damaged middle ear mucosa or other mucosal surfaces, thinned vascular walls, or surgically denuded areas, such as, for example, surgically denuded areas of the pelvis.

The membranes may also be employed as anti-fibroblastic growth barriers, or as nerve coaptation wraps for connecting or repairing severed nerve ends or for repairing inflamed nerves.

The membranes of the present invention may be formed or constructed into various shapes including, but not limited to, flat sheets, tubes, rods or other three dimensional articles, as necessary to facilitate use in a particular application.

A post surgical anti-adhesion barrier or membrane of the present invention is generally used in the form of a sheet of a desired size and shape. A surgeon may cut a custom shape from preformed sheets to suit particular applications. After the membrane is shaped for a suitable fit, the flexible nature of the membrane enables the surgeon to conform the membrane to fit around the area of injury. The membrane can be formed into a strip which wraps around the organ, e.g., an intestine, to prevent formation of adhesions. An anti-adhesion membrane according to the present invention can incorporate ties or straps which connect to the membrane and which are used to tie or otherwise secure the membrane to an area of injury. It is further contemplated that the anti-adhesion membranes of the present invention may be affixed to the wound site by surgical fasteners or sutures. The flexible nature of the present anti-adhesion membrane allows the membrane to flex and bend along with normal movements of the body without being overly restrictive.

Thus, the invention is also directed to a method for reducing post-surgical adhesions. The method involves positioning an adhesion-reducing barrier between the site of surgical activity and neighboring tissues. The adhesion-reducing barrier will contain a biodegradable and/or bioabsorbable membrane. The membrane is preferably the biodegradable and/or bioabsorbable membranes discussed above. The membrane can also be a biodegradable and/or bioabsorbable membrane which contains a plurality of layers, with at least two layers having different biodegradable and/or bioabsorbable fibers from each other or contains sub-micron diameter biodegradable and/or bioabsorbable fibers, having at least one medicinal agent contained within the fibers. Preferably, the membrane will contain an antibiotic.

All embodiments of surgical adhesion barriers or membranes as described herein are well-suited for application by techniques involving endoscopy. Endoscopic surgical procedures involve the use of cannulas or tubes which provide narrow openings into a body and allow minimally invasive access to surgical targets. In laparoscopic procedures, surgery is performed in the interior of the abdomen through small tubes inserted therein. Endoscopes are frequently used as viewing devices inserted through the cannulas which allow surgeons to see the interior of the body.

Certain endoscopic and laparoscopic procedures may require that the surgical region be insufflated. Accordingly, any instrumentation inserted into the body should be substantially sealed to ensure that gases do not enter or exit the body through the incision. Moreover, endoscopic and laparoscopic procedures often require the surgeon to operate on organs, tissues and/or vessels far removed from the incisions. Thus, instruments used in such procedures are typically long and narrow while being functionally controllable from a proximal end of the instrument.

In accordance with the present invention any apparatus for deploying and positioning any of the adhesion barriers or membranes disclosed herein may be inserted through a cannula and deposited at a target site. Once the barrier is positioned as desired, it may optionally be sutured, stapled or otherwise fastened to the target site with instruments designed to be inserted through a cannula.

Thus, in another aspect, the invention is directed to a method of reducing surgical adhesions which involves positioning an adhesion-reducing barrier between the site of surgical activity and neighboring tissue. More specific applications are discussed above.

Nanofiber Fabrication Technique for Biodegradable and/or Bioabsorbable Polymers: Electrospinning Membranes with Different Biodegradable and/or Bioabsorbable Fibers The membranes according to the present invention are preferably produced by electrospinning using a multiple jet system. Preferably, the multiple jet system includes an array of spinnerets for introducing conducting fluid containing the biodegradable and/or bioabsrobable fiberizable material. The use of a multiple jet system to produce membranes in accordance with the invention is possible by having independent control over different jets. Thus, different jets can produce different fibers as discussed more fully above.

Moreover, sub-micron diameter fibers can be produced in accordance with the invention at a relatively high yield. For example, a 40% polymer solution being spun from a single spinneret with a diameter of 700 microns, which results in a final filament having a diameter of 250 nm, will have a draw ratio of $7.84 \times 10^6$. If the extrudate (conducting fluid) from each spinneret has a rate of about 10 $\mu$l/min, the final filament speed will be about 136 m/s for each spinneret, which is a relatively high spinning rate. Thus, a commercially viable process for making membranes according to the invention is achievable with a sufficient number of spinnerets operating at such speeds.

The conducting fluid will preferably include a solution of the polymer materials described more fully above. The polymer material used to form the membrane is first dissolved in a solvent. The solvent can be any solvent which is capable of dissolving the polymer and providing a conducting fluid capable of being electrospun. The solvent is preferably selected from N,N-Dimethyl formamide (DMF), tetrahydrofuran (THF), N-N-dimethyl acetamide (DMAc), methylene chloride, dioxane, ethanol, chloroform or mixtures of these solvents.

The conducting fluid can optionally contain a salt which creates an excess charge effect to facilitate the electrospinning process. Examples of suitable salts include NaCl, $KH_2PO_4$, $K_2HPO_4$, $KIO_3$, KCl, $MgSO_4$, $MgCl_2$, $NaHCO_3$, $CaCl_2$, or mixtures of these salts.

The polymer solution forming the conducting fluid will preferably have a polymer concentration in the range of about 1 to about 80 wt %, more preferably about 10 to about 60 wt %. The conducting fluid will preferably have a viscosity in the range of about 50 to about 2000 mPa·s, more preferably about 200 to about 700 mPa·s.

The electric field created in the electrospinning process will preferably be in the range of about 5 to about 100 kilovolts (kV), more preferably about 10 to about 50 kV. The feed rate of the conducting fluid to each spinneret (or electrode) will preferably be in the range of about 0.1 to about 1000 microliters/min, more preferably about 1 to about 250 microliters/min.

A particular apparatus for producing membranes according to the present invention, which uses a multiple jet electrospinning system, is shown schematically in FIG. 1. Equipment not essential to the understanding of the invention such as heat exchangers, pumps and compressors and the like are not shown.

Referring now to FIG. 1, the conducting fluid, which contains the biodegradable polymer, is supplied by a micro-flow pump system 1. The conducting fluid preferably contains a biodegradable polymer, a solvent and a salt, e.g., 25 wt % PLA-DMF solution with 1 wt % $KH_2PO_4$. Optionally, one or more medicinal agents can be incorporated into the conducting fluid. The pump system 1 is linked to a computer 2 which controls the flow rate of the conducting fluid to selected spinnerets by controlling pressure or flow rate. The flow rate can be changed depending upon the speed of the support membrane 3 and the desired physical characteristics of the membrane, i.e., membrane thickness, fiber diameter, pore size, membrane density, etc.

The pump system 1 feeds the conducting fluid to a multiple jet system 4 that contains manifolds 5 having a bank of spinnerets 6. A charge in the range of about 20 to about 50 kV is typically applied to the spinnerets by a high voltage power supply 7. A hood 8 is positioned over the multiple jet system 4 to remove the solvent at a controlled evaporation rate.

A ground plate 9 is positioned below the multiple jet system 4 such that an electric field is created between the charged spinnerets 6 and the ground plate 9. The electric field causes tiny jets of the conducting fluid to be ejected from the spinnerets and spray towards the ground plate 9, forming small, e.g., sub-micron, diameter filaments or fibers.

A moving support 3 is positioned between the charged spinnerets 6 and the ground plate 9 to collect the fibers which are formed from the spinnerets and to from an interconnected web of the fibers. The support 3 moves in the direction from the unwind roll 10 to the rewind roll 11.

The micro-flow control/pumping system is electrically isolated from the ground and is powered by an isolation transformer 12.

The post-spinning processors 13 have the functions of drying, annealing, membrane transfer (for example, from a stainless steel mesh substrate to another substrate, e.g., a Malox mesh) and post conditioning.

Multiple jets with designed array patterns can be used to ensure the fabrication of uniform thickness of the membrane. Hood, heating and sample treatment chambers can also be included to control the solvent evaporation rate and to enhance the mechanical properties. The recovered thickness can be precisely controlled from tens of microns to hundreds of microns. While additional embodiments or modifications to the electrospinning process and apparatus are described below, a more detailed description of an apparatus and method for electrospinning polymeric fibers is set forth in co-pending, commonly owned patent application, Ser. No. 09/859,004, entitled "Apparatus and Methods for Electrospinning Polymeric Fibers and Membranes," filed on May 16, 2001 and incorporated herein for all purposes by reference.

Variation of Electric/Mechanical Properties of Conducting Fluid

The properties of the resulting membrane produced by electrospinning will be affected by the electric and mechanical properties of the conducting fluid. The conductivity of the macromolecular solution can be drastically changed by adding ionic inorganic/organic compounds. The magneto-hydrodynamic properties of the fluid depend on a combination of physical and mechanical properties, (e.g., surface tension, viscosity and viscoelastic behavior of the fluid) and electrical properties (e.g., charge density and polarizability of the fluid). For example, by adding a surfactant to the polymer solution, the fluid surface tension can be reduced, so that the electrostatic fields can influence the jet shape and the jet flow over a wider range of conditions. By coupling a pump system that can control the flow rate either at constant pressure or at constant flow rate, the effect of viscosity of the conducting fluid can be controlled.

Electrode Design

In another method for producing membranes according to the present invention, the jet formation process during electrospinning is further refined to provide better control over fiber size. Instead of merely providing a charged spinneret and a ground plate, a positively charged spinneret is still responsible for the formation of the polymer solution droplet and a plate electrode with a small exit hole in the center is responsible for the formation of the jet stream. This exit hole will provide the means to let the jet stream pass through the plate electrode. Thus, if the polymer droplet on the positively charged spinneret has a typical dimension of 2–3 mm and the plate electrode is placed at a distance of about 10 mm from the spinneret, a reasonable electrostatic potential can be developed. The short distance between the two electrodes implies that the electrostatic potential could be fairly low. However, the resultant electric field strength could be sufficiently strong for the electrospinning process. By varying the electric potential of individual spinnerets, the jet formation can be controlled and adjusted for individual spinnerets. Such an electrode configuration should greatly reduce the required applied potential on the spinnerets from typically about 15 kilovolts (kV) down to typically about 1.5 to 2 kV (relative to the ground plate potential). The exact spinneret potential required for stable jet formation will depend on the electric/mechanical properties of the specific conducting fluid.

Control of Jet Acceleration and Transportation

In another method for producing membranes according to the present invention, the jet stream flight of individual spinnerets is also precisely controlled. The jet stream passing through the plate electrode exit hole is positively charged. Although this stream has a tendency to straightening itself during flight, without external electric field confinement the jet will soon become unstable in its trajectory. In other words, the charged stream becomes defocused, resulting in loss of control over the microscopic and macroscopic properties of the fluid. This instability can be removed by using a carefully designed probe electrode immediately after the plate electrode and a series of (equally) spaced plate electrodes. The electrode assembly (i.e., the probe electrode and the plate electrodes) can create a uniform distribution of electrostatic potential along the (straight) flight path. The acceleration potential is formed by placing the base potential of the spinneret at about +20 to +30 kV above the target (at ground potential) while the electrostatic potential of the probe electrode can be adjusted to slightly below the plate electrode base potential. The composite electrodes are capable of delivering the jet stream to a desired target area.

Jet Manipulation

In yet another method for producing membranes according to the present invention, individual jet streams can be focused by using an "Alternating Gradient" (AG) technique. The basic idea is to use two pairs of electrostatic quadrupole lenses. The second lens has the same geometric arrangement as the first lens with a reversed (alternate) electric gradient. The positively charged jet stream will be focused, for example, in the xz plane after the first lens and then be refocused in the xz plane after the second lens. It is noted that the z-direction represents the direction of the initial flight path. By applying an additional triangle-shaped waveform to the potential on one of the pairs of the quadrupole, the jet can be swept across the target area, allowing the control of the direction of the jet stream. Furthermore, with varying waveform of the 'sweep' potential, a desired pattern on the target can be formed.

Pattern Design by Electrospinning

Figure 2:
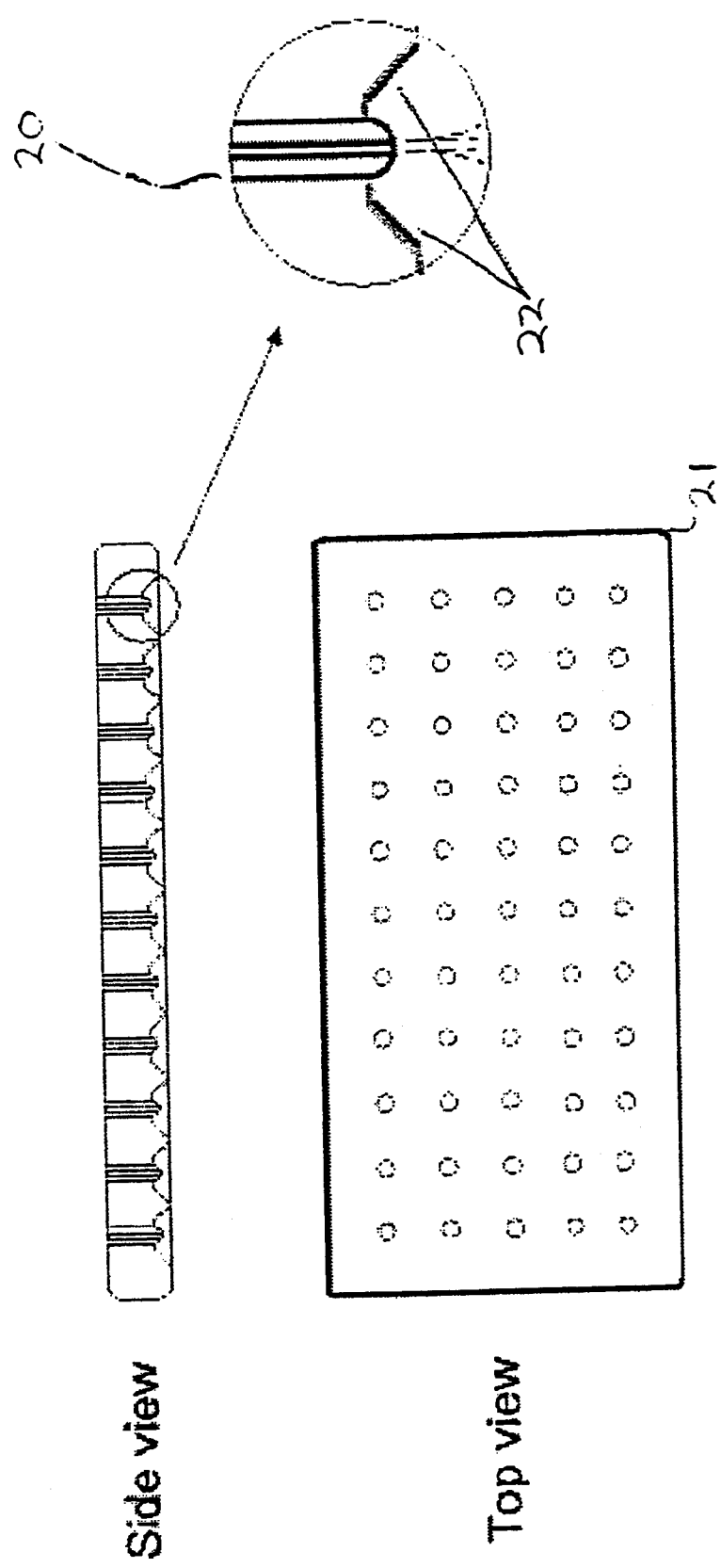
FIG. 2 is a schematic of an array of spinnerets for an electrospinning process.

In yet another method for producing membranes according to the present invention, reference will be made to FIG. 2. In this method, the conducting fluid is introduced into the electrospinning process through an array of electrospinning spinnerets 20. The array of electrospinning spinnerets are assembled in a matrix 21 that provides electrical isolation for the spinnerets, with each spinneret having two pairs (X and Y direction) of miniature scanning electrodes 22. The spinneret 20 and the scanning electrodes 22 are electrically wired such that each individual polymer solution jet can be turned on and off and be steered to a finite size target area. As each spinneret 20 can be turned on/off independently by electricity, the response time will be relatively fast. Also, each spinneret 20 can deliver a different solution, e.g., each containing a different polymer or different drug or concentration of drug. A designed pattern can be obtained in the resultant membrane. This pattern can be precisely controlled by a computer and can be tailored for specific medical applications.

Multiple Jet Slit-Die Geometry

Figure 3:
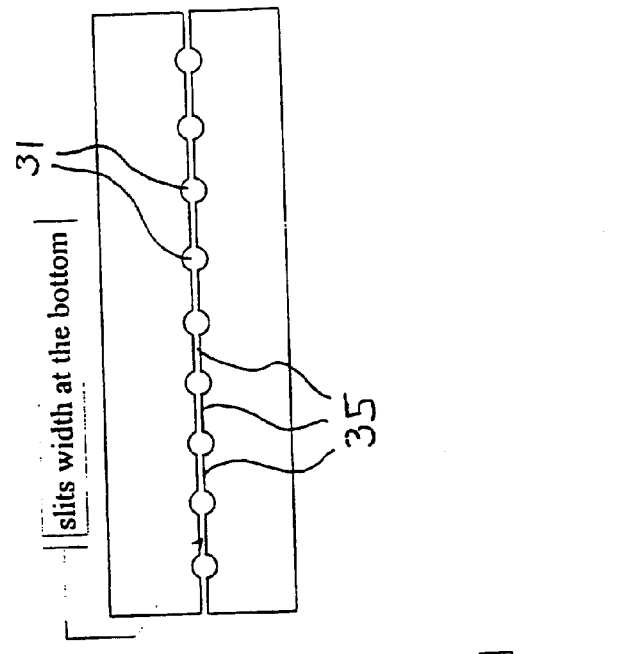
FIG. 3(a) is a side view schematic of a multiple spinneret system for producing membranes in accordance with the invention.
FIG. 3(b) is a cross-sectional view of the spinneret system of FIG. 3(a) as seen along viewing lines IV—IV thereof.
FIG. 3(c) is a bottom view of the multiple spinneret system of FIG. 3(a).

In another apparatus for producing membranes in accordance with the present invention, reference is made to FIGS. 3(a)–3(c). In this apparatus, a multiple jet system 30 comprises an array of electrospinning spinnerets 31, each spinneret 31 being defined by a slit 32 formed in a slit-die 33 that is coupled to high voltage to serve as an electrode disposed above the ground plate 34. As shown in detail in FIG. 3(c), the spinnerets 31 are each interconnected by selectively narrow slits 35, such that each spinneret 31 is interconnected to a neighboring spinneret 31 by a slit 35. The conducting fluid will not flow through the slits 35, but will flow through each of the spinnerets 31 in a more robust manner.

The slit-die approach permits three distinct advantages that are not available by using individual spinnerets. (1) The slit-die is made up of two separate components with controlled dimensions of the effective openings for the spinnerets. In other words, by changing the distance between the two components, the effective openings of the spinnerets become available. (2) The presence of slits between the larger openings permits fluid flow and thereby equalizes the pressure difference between the spinnerets. (3) The presence of slits can also reduce potential blockage of the fluid.

The membranes produced by the slit-die approach can achieve a larger degree of flexibility in the structures. For example, different size nanofibers can be produced from the same slit-die setup.

Control of Degradation Rate Through Processing Parameters

As discussed above, very different fiber diameter and morphology in the membrane can be obtained by changing the parameters in the electrospinning process. As the degradation rate is inversely proportional to the fiber diameter, the manipulation capability through processing parameters provides not only the means to control the degradation rate of the membrane but also the ways to control drug loading efficiency and the drug release rate.

Figure 5:
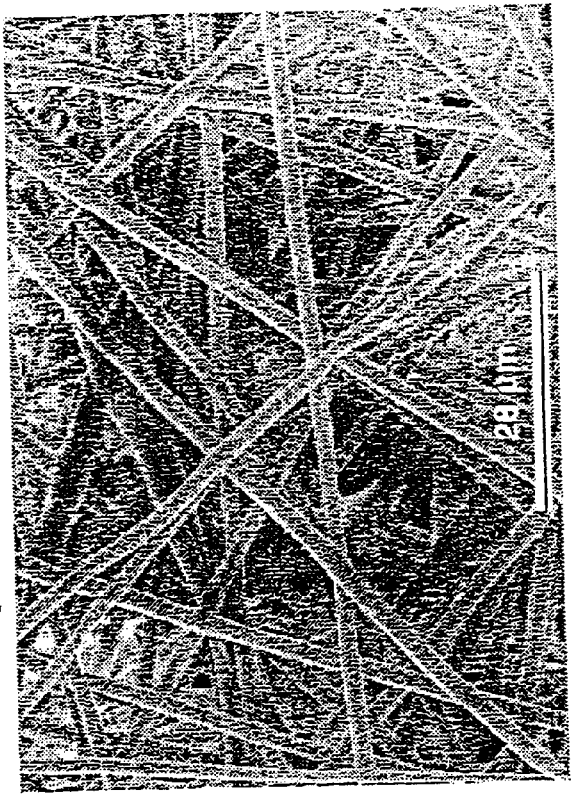
FIG. 5 is an SEM of a PLA-co-PGA membrane spun from a solution without salt added.
Figure 4:
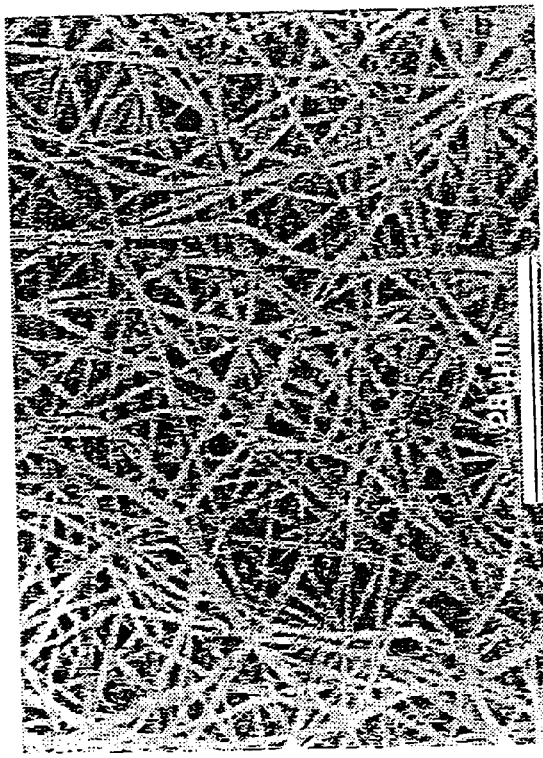
FIG. 4 is an SEM of a PLA-co-PGA membrane spun from a solution containing 1 wt % $KH_2PO_4$.

For example, it is believed that a change in charge density (through the addition of salts) can significantly affect the fiber diameter. When 1 wt % potassium phosphate ($KH_2PO_4$) was added to a PLA-co-PGA solution, the fiber diameter became much thinner (see SEM picture in FIG. 4) than the one with no salt added (FIG. 5). Thus, it is believed that higher excess charge density generally favors the production of thinner fibers and lower excess charge density favors the production of thicker fibers. Several other kinds of salts (e.g. NaCl, $KH_2PO_4$, KIO and $K_3PO_4$), which are all biologically compatible to the body, are also contemplated.

Control of Drug Release Rate and Test of Antibacterial Effect

It is also believed that when a drug is incorporated into the fibers of the membrane, the drug release rate is a function of fiber diameter. As such, the release rate of a drug trapped in the membrane can be precisely controlled. Many surgical procedures often lead to adhesion formation involving the colon and rectum. This additionally increases the risk of post-operative infection. The addition of antibiotics to the membrane with scheduled release may be used to reduce the risk of abscess and infection.

EXAMPLES

The following non-limiting examples have been carried out to illustrate preferred embodiments of the invention. These examples include the preparation of membranes according to the invention, analysis of the membranes and testing of the membranes.

Example 1

Figure 6:
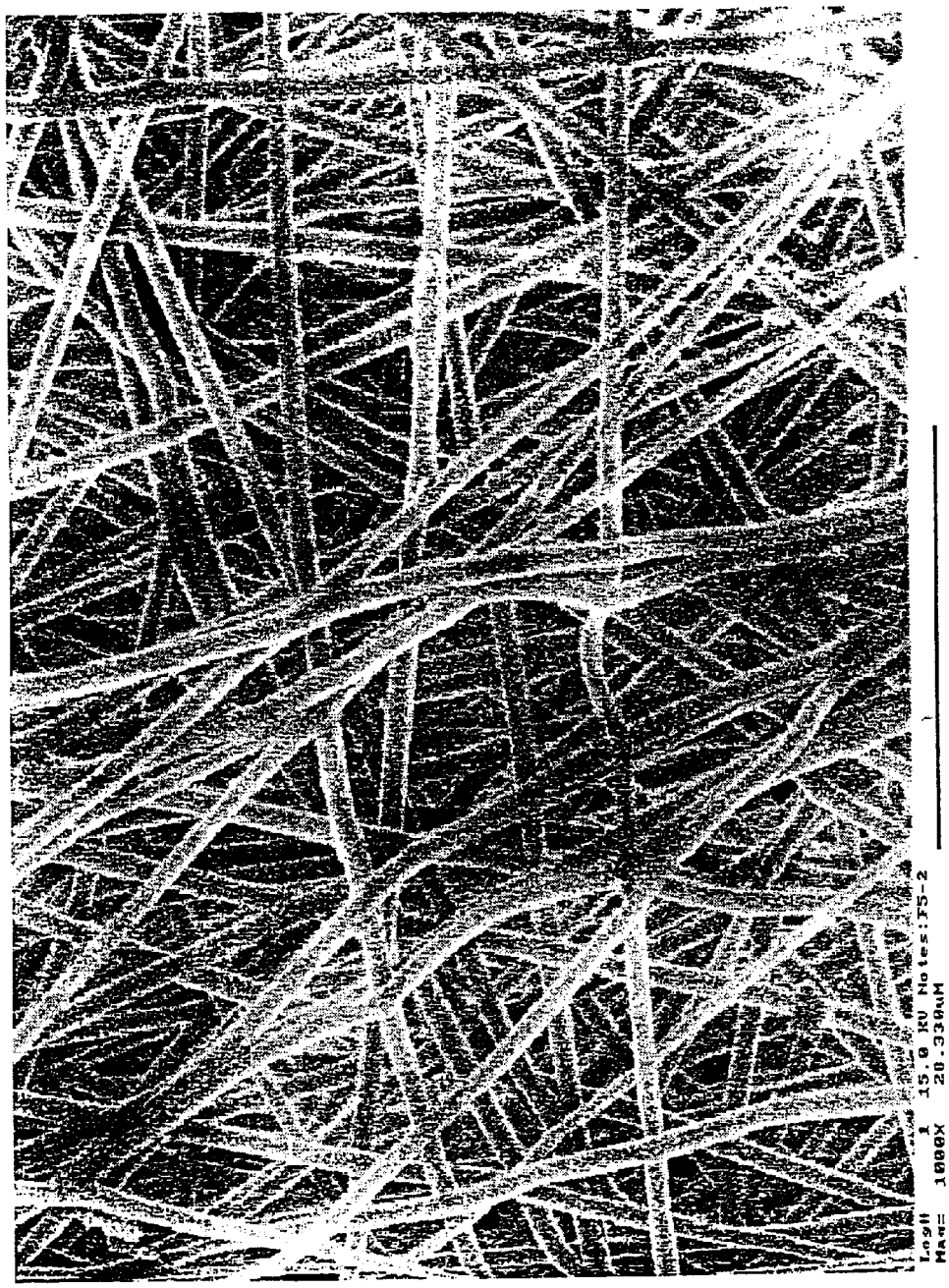
FIG. 6 is an SEM of a membrane described in Example 1.

A membrane was prepared as follows: a 30 wt % PLG copolymer/DMF solution was prepared by slowly dissolving PLG copolymer pellets (inherent viscosity of 0.55–0.75. Birmingham Polymers Inc., AL) into an N,N-dimethyl formamide (DMF) solvent at room temperature. The solution was then loaded into the 5 ml syringe fitted with a gauge 20 needle, and delivered through a Teflon tube (0.03" ID) to the exit hole of an electrode having a diameter of 0.025". The solution was pumped and controlled by a syringe pump (Harvard Apparatus "44" series, MA) at a flow rate of 20 microliters/min. A 25 kV positive high voltage (by Glassman High Voltage Inc.) was applied on the electrode. The distance from the tip of the electrode to the grounded collecting plate was 15 cm. A tiny electrospinning jet was formed and stabilized in 30 seconds under these conditions. The collecting plate was movable and controlled by a stepper motor. The collecting plate was continually moved at a rate of 1 mm/sec until a membrane having a relatively uniform thickness of about 100 microns was obtained. An SEM (Scanning Electron Microscopy) image of the membrane is shown in FIG. 6.

Example 2

A biodegradable and bioabsorbable membrane according to the present invention, fabricated by a multi-jet electrospinning process, was prepared as follows: an 8 wt % polyacrylonitrile (Aldrich Chemical Company, Inc.)/DMF solution was prepared by slowly adding and dissolving the polymer powders into an organic solvent, which was DMF (N,N-dimethyl formamide), at room temperature. After the solution was completely mixed, it was then loaded into 6 individual syringes, each with a volume of 5 mL. The syringes were fitted with gauge 20 needles and the solution was delivered through Teflon tubes (0.03" ID) to 6 electrodes, each having a tiny hole with a diameter of 0.025". The polymer solution was finally pumped and controlled by a syringe pump (Harvard Apparatus "44" series, MA) at a flow rate of 25 microliters/min. In addition, a 26 kV positive high voltage (by Glassman High Voltage Inc.) was applied on the electrodes in order to obtain the existence of six well-stabilized electrospinning jets. The distance from the tip of the electrodes to the grounded collecting plate was 15 cm and the tips of the electrodes were spaced about 2 cm apart from each other. Closer spacing between electrodes (spinnerets) could have been achieved by changing appropriate parameters, e.g., by increasing the applied electric potential. The collecting plate was movable and controlled by a step motor. The collecting plate was continually moved at a rate of 1 mm/sec until a bioabsorable and biodegradable membrane having a relatively uniform thickness of about 100 microns was obtained.

Example 3

A polymer solution suitable for electrospinning, which contained a drug, was prepared as follows: A sample of Poly(DL-lactide) ("PLA") purchased from Birmingham Polymers, Inc., Birmingham, Ala. (Product No. D98120) having a weight average molecular weight of $1.09 \times 10^5$ g/mole and a polydispersity of 1.42 was stored in a vacuum oven at room temperature. The pellets were dissolved in DMF purchased from Fisher Scientific, Fair lawn, N.J. to form a 25 wt % solution. The antibiotic drug used was Mefoxin™ from Merck & Co., Inc., West Point, Pa. The antibiotic was dissolved in distilled water and then mixed with PLA/DMF solution in appropriate amounts to form the solution with a PLA/drug ratio of 9:1. A stable jet was formed using this solution in the electrospinning process described in Example 1.

Example 4

Figure 7:
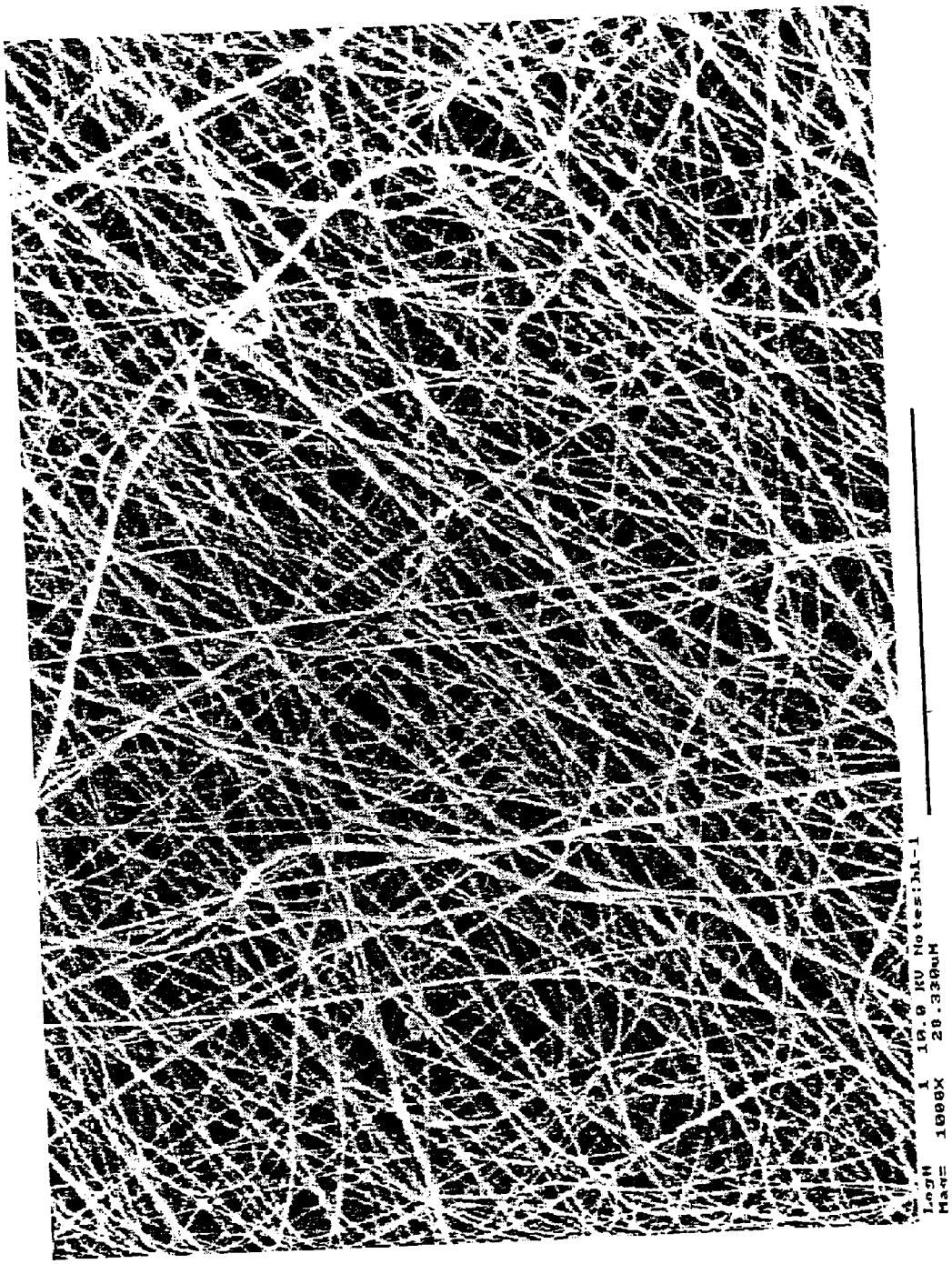
FIG. 7 is an SEM of a membrane described in Example 4.

A second membrane was prepared in a similar manner to Example 1, except that a drug solution was added to the polymer solution prior to electrospinning and the voltage applied to the electrode was adjusted. The drug solution was prepared by dissolving 0.6 grams of Mefoxin (Merck & Co Inc.) into 0.4 grams of water. The drug solution was then very slowly (dropwise) added to the polymer solution with gentle stirring until it reached a final PLG/drug ratio of 19:1. A 20 kV positive high voltage (by Glassman High Voltage Inc.) was applied on the electrode. All other parameters were the same as Example 1. An SEM (Scanning Electron Microscopy) image of the membrane containing the drug is shown in FIG. 7.

Figure 8:
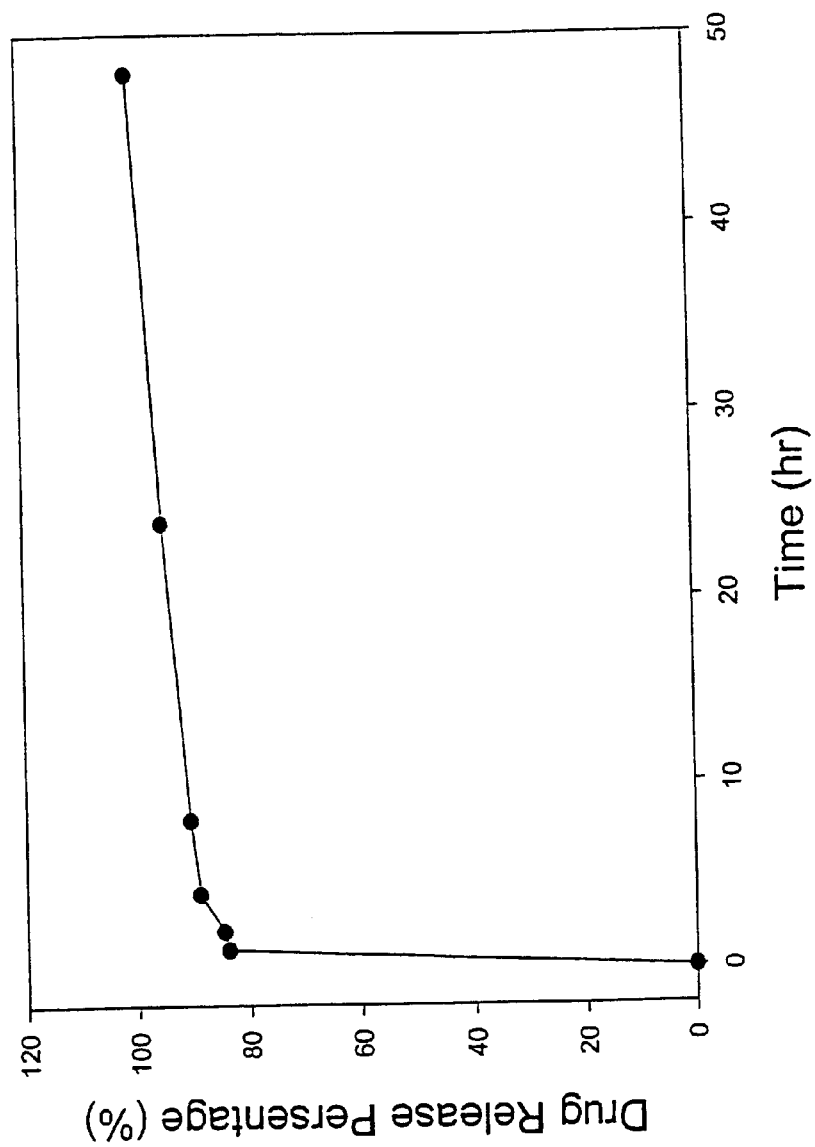
FIG. 8 is a graph of the results of the drug release test described in Example 4.

The drug release rate was determined by placing the membrane in a phosphate buffer solution (PBS) and then by monitoring the drug concentration in the buffer solution vs. time using an ultra violet (UV) light (234 nm) absorption measurement. The drug release (in PBS buffer) profile is shown in FIG. 8.

Example 5

Figure 9:
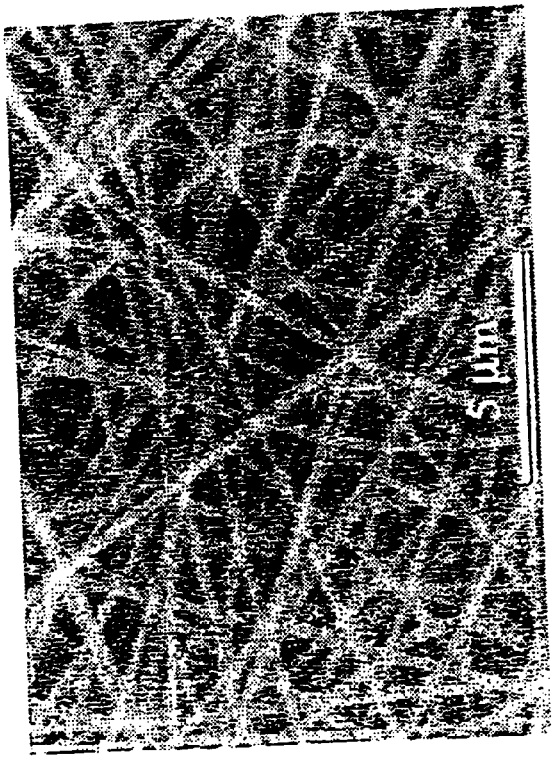
FIG. 9 is an SEM of a PLA membrane described in Example 5.

A membrane was fabricated as follows: A 35 wt % PLA polymer/DMF solution was prepared by slowly dissolving the PLA pellets. The solution was fed through the syringe pump system to the electrodes at a flow rate of 20 microliters/min per jet. A 25 kV positive high voltage was applied to the electrode. FIG. 9 shows a typical scanning electron microscopy (SEM) image of an electrospun PLA membrane made by the procedures described above. It has an average fiber diameter of 200 nm. The typical membrane density is about 0.25 g/cm$^3$, as compared to the neat resin (PLA) density of 1.3 g/cm$^3$.

Example 6

Figure 10:
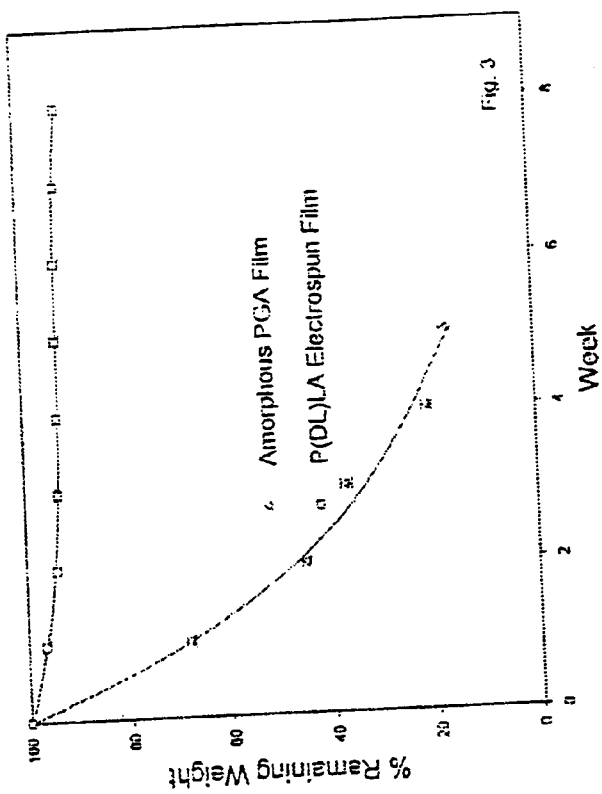
FIG. 10 is a graph of the results of the biodegradation tests described in Example 6.

An in-vitro biodegradation test was conducted to evaluate the performance of electrospun membranes. The biodegradation test was conducted using the following method, which is routinely used in the suture industry: a PGA membrane was submerged in a buffer solution containing sodium phosphate, potassium phosphate, and distilled water (pH 7.3), and maintained at 37° C. The weight loss was measured as a function of time. The test was repeated for a PLA membrane. The results for both membranes are plotted in FIG. 10. A review of FIG. 10 reveals that the major weight loss (50%) varies from 2 weeks (PGA) to about 6 months (PLA).

Example 7

A membrane containing dual thickness fibers was prepared as follows: a 25 wt % PLA-DMF solution was prepared by slowly dissolving PLA polymer pellets having the same molecular weight and poly dispersity as in Example 3 into a DMF solvent. A drug solution was prepared by dissolving 0.6 grams of Mefoxin (Merck & Co Inc.) into 0.4 grams of water. The drug solution was then very slowly (dropwise) added to the polymer solution with gentle stirring until it reached a final PLA/drug ratio of 19:1. A 20 kV positive high voltage (by Glassman High Voltage Inc.) was applied on the electrode. All other parameters were the same as Example 1. A membrane having a network structure consisting of large size filaments (2 micron diameter), very fine fibrils (50 nanometer diameter) and small blobs was obtained by varying the solution feed rate over a range from 20 $\mu$l/min to 70 $\mu$l/min. An SEM of the resulting membrane is shown in FIG. 11.

The membrane was then placed in the buffer solution described in Example 6. After one week of degradation in the control buffer, the fine fibers completely disappeared (FIG. 12). A comparison of FIGS. 11 and 12 reveals that this morphology results in a rapid weight loss in the first week. Thus, if more rapid weight loss is desired, a membrane having a higher concentration of thin fibrils can be produced.

Example 8

An experiment was conducted to evaluate the barrier properties of different membranes for preventing post-operative induced adhesions. The experiment used an objective rat model (ORM) to evaluate the performance of electrospun PLA-co-PGA membranes, with and without an antibiotic drug (Mefoxin) contained in the membrane structure, which were prepared in the same manner as in Examples 1 (without the drug) and 4 (with the drug). A control group was also used for comparison.

The test procedures used were as follows: the membrane being tested was first sterilized using $^{60}$Co radiation source. The membrane sample was sealed in a plastic bag in a container filled with dried nitrogen gas. The package then received γ-radiation doses from 5.15~25 kGy, depending on the mass. This procedure has been well documented in the literature.

300–450 gram male Sprague-Dawley rats were used in the experiments. They were individually housed and given food and water ad libitum both pre- and postoperatively. Anesthesia was produced using an IM ketamine (80 mg/kg) and xylaxine (10 mg/kg) injection into the right hindleg prior to the celiotomy. Euthanasia was performed using intracardiac injection of pentobarbital (60 mg/kg).

The rats were divided into two procedure groups. The first group underwent a midline celiotomy and the cecum identified and scored using an abrasive pad until serosal bleeding was noted on the anterior surface. A 1×1 cm square of abdominal wall muscle was then excised directly over the cecal wound. The first group experiment was conducted using 12 animals with the membrane and 14 animals with the membrane containing antibiotics, which were compared to 12 control animals (cecal abrasions and buttons without any membrane). The celiotomy was then closed in two layers immediately (control, n=12), after a barrier was laid in between the cecum and the abdominal wall (n=12), or after an antibiotic-impregnated barrier was placed in the aforementioned are (n=14). All rats underwent a second celiotomy after 4 weeks. The presence or absence of adhesions from the cecum to the abdominal wall was noted. The cecum was then isolated from the rest of the bowel and the breaking strength of the adhesion was measured by using a tensiometer.

Figure 13:
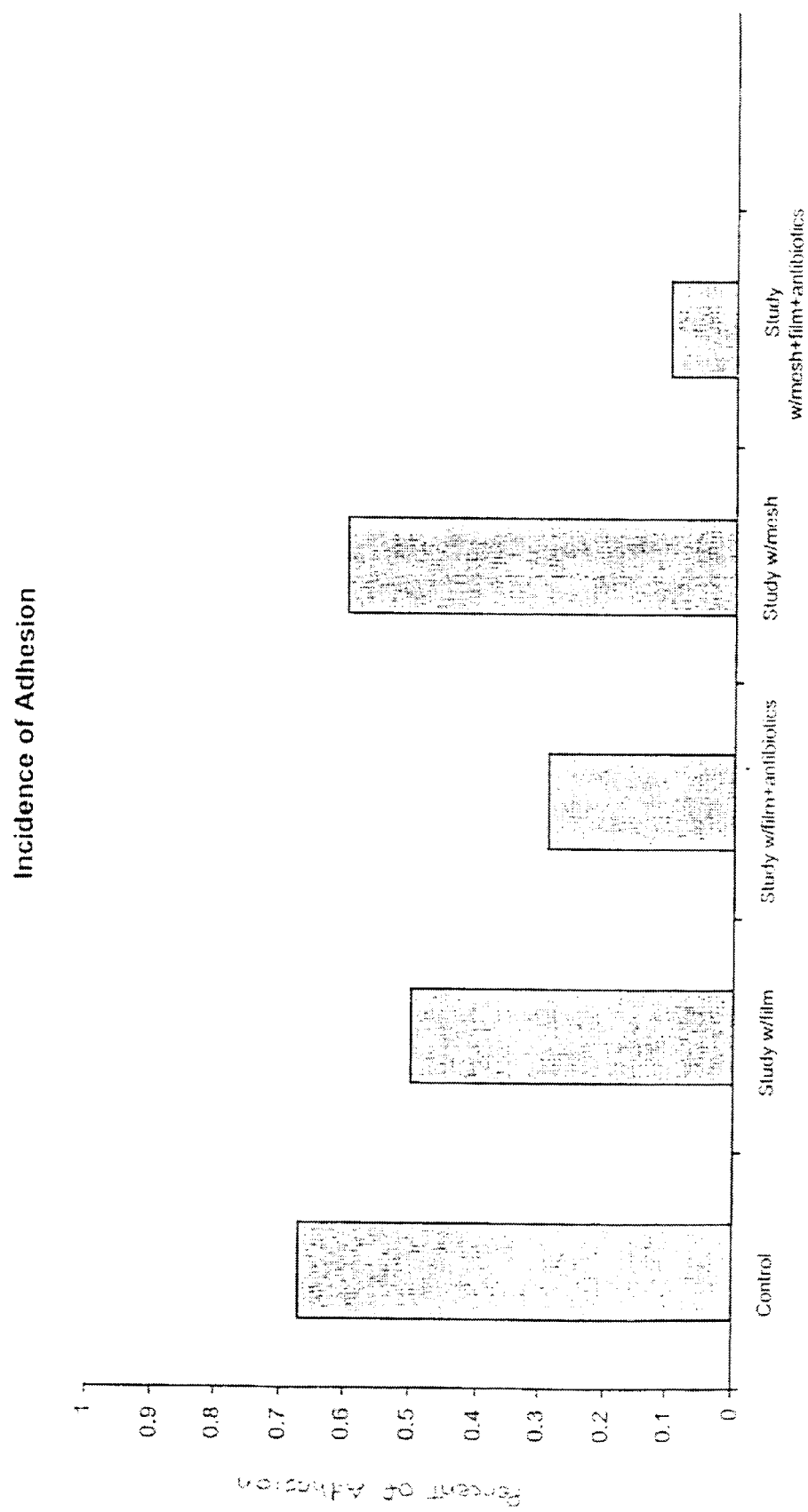
FIG. 13 is a graph of the results of the adhesion experiment described in Example 8.
Figure 14:
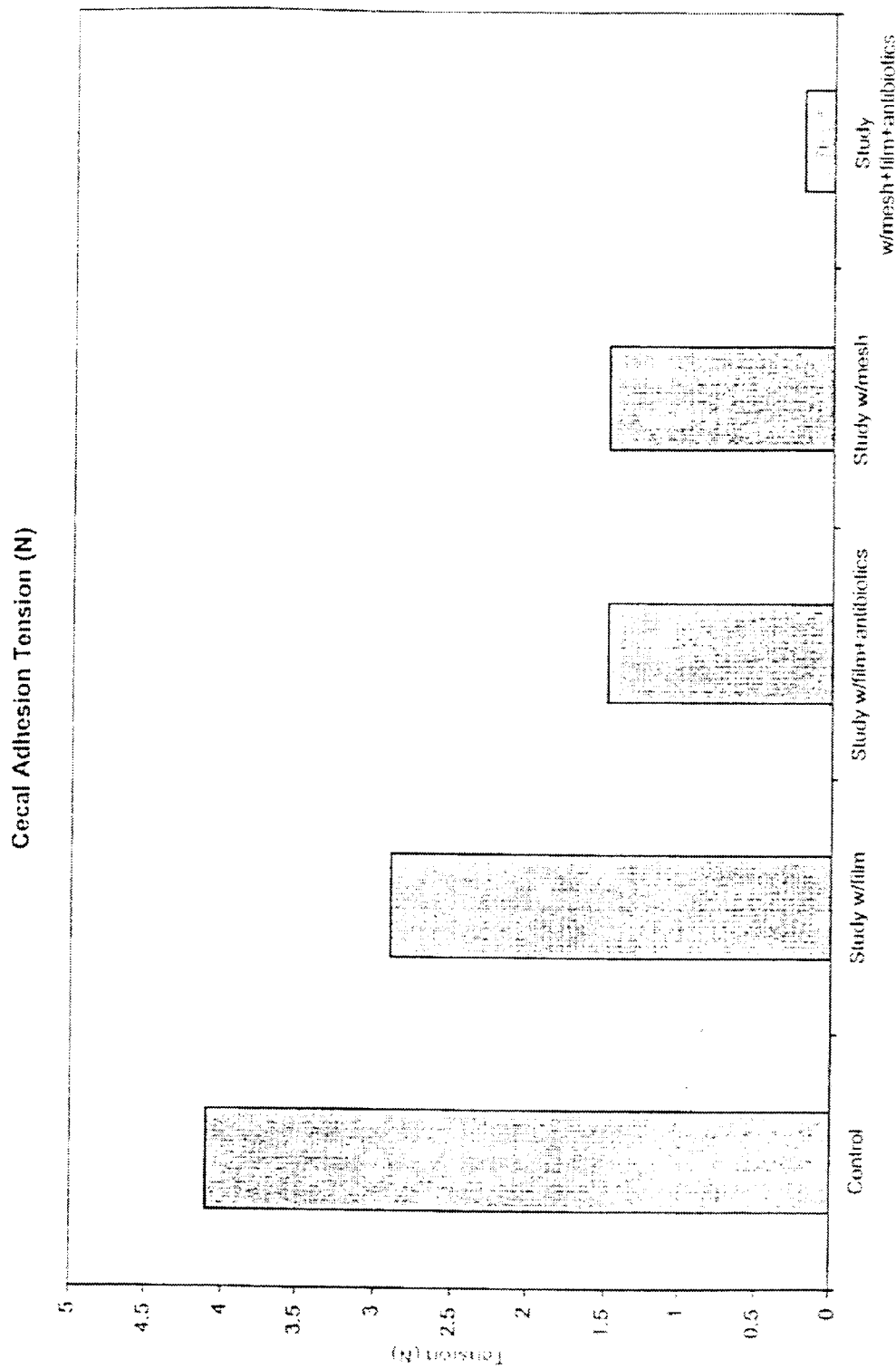
FIG. 14 is a graph showing the tensiometer readings from the experiment described in Example 8.

In the first group of experiments, cecal adhesions were noted in 67% of the control set, 50% of the set with barriers, and 38% of the set with barriers impregnated with antibodies (see FIG. 13). Tensiometer readings on those adhesions present were found to be 6.18, 5.76, and 4.30 respectively (see FIG. 14). Only adhesions from the cecum to the abdominal wall were counted. Adhesional bands between the bowel and other abdominal organs were noted on occasion, but were not taken into account.

In the second group experiment, Marlex mesh, a material often used in abdominal surgery to repair the abdominal wall, was used to test the membranes. This mesh has the severe complication of causing adhesions to the intestines which not only leads to bowel obstruction, but also fistula formation. Both complications can be devastating to patients. The Marlex mesh was applied to a defect created in the abdominal wall and 10 animals had the barrier membrane interposed between the mesh and the intestines, while 10 controls had the Marlex placed with no interposing membrane. The second group of rats had Marlex mesh placed into the abdominal cavity. The abdomen was opened using a midline celiotomy and a 1×1 cm square of Marlex mesh was placed over the cecum and fixed to the abdominal wall using two silk sutures. The abdomens were then either immediately closed in two layers (control, n=10) or had a barrier placed in between the cecum and the mesh (n=10). All animals underwent a second celiotomy after 4 weeks. The presence or absence of adhesions between the cecum and mesh were noted.

In the group of rats with Marlex mesh, the first set of rats all has adhesions from the cecum to the mesh (100%). The mesh also has a multitude of other adhesions to the omentum, stomach, and liver making a measurement of adhesional strength from cecum to abdominal wall problematic. The set with barriers was found to have only one rat with adhesions from the cecum to the abdominal wall (10%).

Overall, the test results showed good barrier properties of the membranes, i.e., a low incidence of induced adhesion in the membrane embedded area, while an adhesion was induced in the control area. The membrane containing the antibiotic showed better barrier properties than the membrane without the antibiotic.

Example 9

The antibacterial effect of drug containing membranes was tested using the following procedures: 8 ml of Luria Broth (LB) and 80 microliters of *E. coli* cells were added to each of four sample test tubes. A 7.0×7.0 cm sample of a PLA electrospun membrane having a thickness of about 75 microns (with a corresponding total weight of 100 mg) was added to one of the test tubes. A second sample of a PLA membrane containing approximately 4.83 mg of Mefoxin was added to another test tube. A third sample of a PLA membrane containing approximately 8.85 mg of Mefoxin was added to a third test tube. The last test tube was used as a control.

LB was used to grow the *E. coli* bacterial cells. The sample tubes were placed in an incubator overnight. The temperature of the incubator was set at 37° C. and the shaking rate was set at 225 rpm. Shaking was necessary in order for the *E. coli* bacteria to receive enough nutrients needed to grow. Using a SmartSpec *3000 instrument, the optical density (OD) at the 600 nm wavelength for *E. coli* bacteria was recorded and the amount of cells in each test tube was calculated. The cell concentration could be related to the product of the optical density of each sample and a conversion factor. As the optical density increases (the broth becomes more turbid), the cell concentration should increase. The results are shown in FIG. 15, with the y-axis unit being cell/ml or the bacteria concentration.

Figure 15:
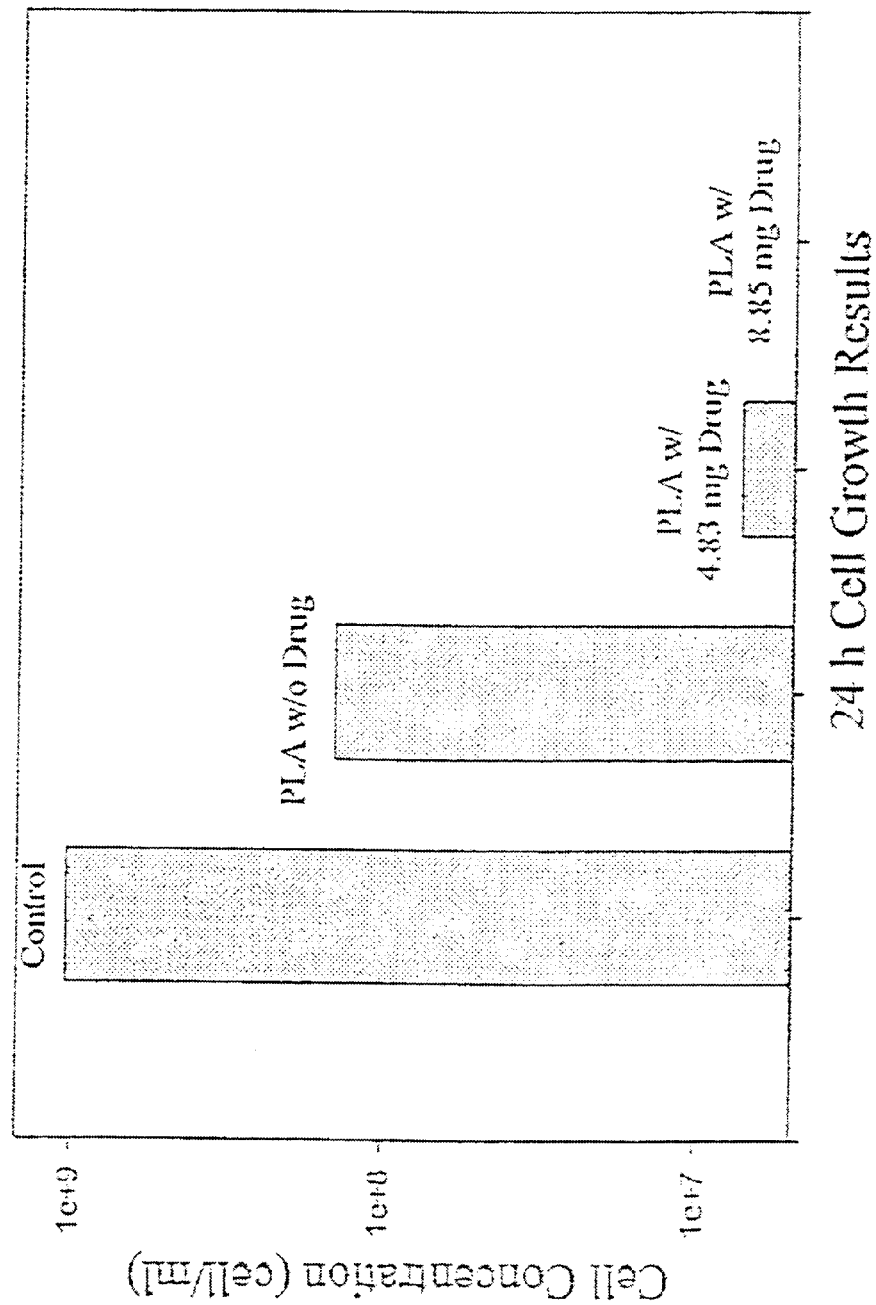
FIG. 15 is a graph of the results of the antibacterial test described in Example 9.

A review of FIG. 15 reveals that the growth of *E. coli* bacteria is completely prohibited by the release of the Mefoxin antibiotic drug from the membrane containing 8.85 mg of the drug. Also, it appears that the higher the loading concentration of Mefoxin, the more effective the membrane becomes.

Example 10

An in-vivo biodegradation test was conduced using a PLA electrospun membrane having an average fiber diameter in the range of about 100–150 nanometers. The membrane was fabricated as follows. A 25 wt % PLA solution in DMF was prepared. A 60 wt % Mefoxin drug in aqueous solution was then added to the polymer solution to reach a final PLA/drug ration of 9:1. A 20 kV positive voltage was applied to the electrode. An SEM of the initial as spun membrane (FIG. 16) shows smooth fibrous structures with an average fiber diameter between 100–150 nm. The membrane was implanted into a rat and removed after one week, following the procedures described in Example 8. An SEM of the partially biodegraded membrane is shown in FIG. 17.

Figure 17:
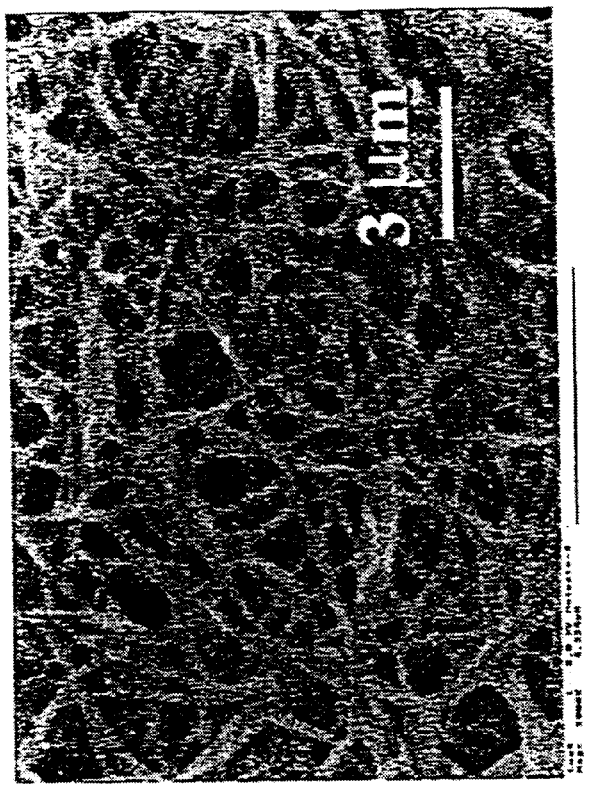
FIG. 17 is an SEM of the partially biodegraded membrane described in Example 10.
Figure 16:
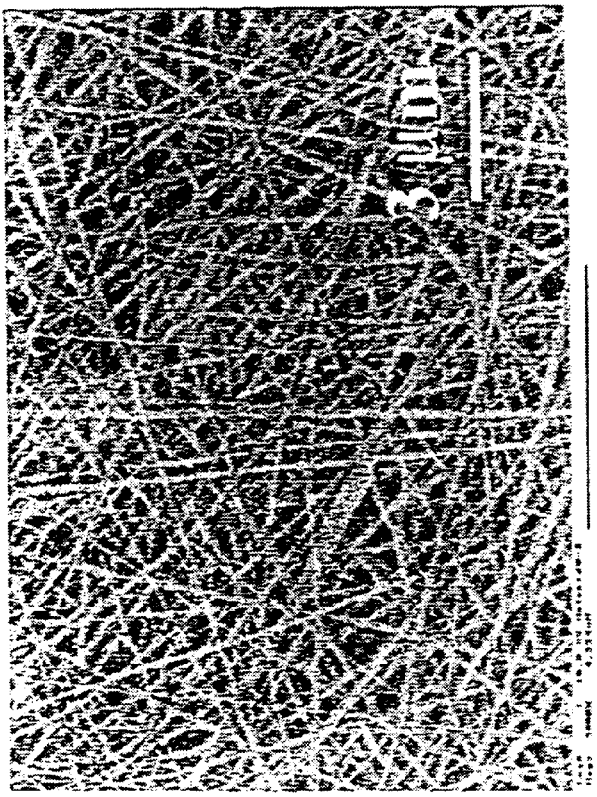
FIG. 16 is an SEM of the as spun membrane described in Example 10.

A comparison of FIGS. 16 and 17 reveals that the morphology of the membrane has been changed, resulting in a more porous structure.

Example 11

A bioabsorbable composite membrane consisting of two polymer components of different hydrophobicity according to the present invention was prepared as follows: First, a 6 wt % polyethylene oxide (PEO)/DMF solution was prepared by slowly adding the polymer powders into an organic solvent, which was DMF (N,N-dimethyl formamide). Second, a 30 wt % polylactide glycolide (PLG)/DMF solution was made by dissolving the polymers into DMF as well. After these two solutions were each completely homogenized at the room temperature, they were then loaded separately into two individual syringes, each with a volume of 5 mL. Next, the syringes were fitted with 2 gauge 20 needles and delivered through Teflon tubes to the electrodes, each having a tiny hole with a diameter of 0.025". The polymer solutions were finally pumped and controlled by a syringe pump at a flow rate of 20 microliters/min. In addition, a 25 kV positive high voltage was applied on two separate electrodes in order to obtain the existence of well-stabilized electrospinning jets. The distance from the tips of the electrodes to the ground collecting plate was 15 cm. Furthermore, a step motor was utilized in order to control the movement of the ground collector so that it was capable to move in different directions, either left or right. The collecting plate was moving at a rate of 5 steps/sec continuously until a bioabsorable membrane having a relatively uniform thickness of 100 microns was achieved.

Example 12

A bioabsorbable composite membrane consisting of two component polymer blend of different hydrophobicity according to the present invention was prepared as follows: First, a 2 wt % polyethylene oxide (PEO, Mw=100,000 g/mol)/DMF solution was prepared by slowly adding the polymer powders into an organic solvent, which was DMF (N,N-dimethyl formamide). Second, a 20 wt % polylactide glycolide (PLG)/DMF solution was made by dissolving the polymers into DMF as well. These two solutions were mixed together and were each completely homogenized at the room temperature. They were then loaded separately into two individual syringes, each with a volume of 5 mL. Next, the syringes were fitted with 2 gauge 20 needles and delivered through Teflon tubes to the electrodes, each having a tiny hole with a diameter of 0.025". The polymer solutions were finally pumped and controlled by a syringe pump at a flow rate of 20 microliters/min. In addition, a 25 Kv positive high voltage was applied on two separate electrodes in order to obtain the existence of well-stabilized electrospinning jets. The distance from the tips of the electrodes to the ground collecting plate was 15 cm. Furthermore, a step motor was utilized in order to control the movement of the ground collector so that it was capable to move in different directions, either left or right. The collecting plate was moving at a rate of 5 steps/sec continuously until a bioabsorable membrane having a relatively uniform thickness of 100 microns was achieved.

Thus, while there has been disclosed what is presently believed to be preferred embodiments of the invention, those skilled in the art will appreciate that other and further changes and modifications can be made without departing from the scope or spirit of the invention, and it is intended that all such other changes and modifications are included in and are within the scope of the invention as described in the appended claims.

We claim:

1. A system for controlled delivery of a medicinal agent comprising a medicinal agent to be delivered and a biodegradable and/or bioabsorbable fibrous article physically associated with said medicinal agent to release said agent at a controlled rate, said fibrous article comprising a composite of different biodegradable and/or bioabsorbable fibers or an asymmetric composite of different biodegradable and/or bioabsorbable fibers.

2. A system according to claim 1, wherein different fibers refers to fibers of different diameters.

3. A system according to claim 2, wherein said fibers of different diameters include fibers having diameters less than 1 micron and fibers having diameters greater than 1 micron.

4. A system according to claim 3, wherein said fibrous article comprises at least about 20 weight percent of sub-micron diameter fibers.

5. A system according to claim 4, wherein said fibrous article comprises at least about 50 weight percent of sub-micron diameter fibers.

6. A system according to claim 1, wherein different fibers refers to fibers of different biodegradable and/or bioabsorbable materials.

7. A system according to claim 1, wherein different fibers refers to fibers of different diameters and different biodegradable and/or bioabsorbable materials.

8. A system according to claim 1, wherein said biodegradable and/or bioabsorbable fiberizable material comprises a biodegradable and/or bioabsorbable polymer.

9. A system according to claim 8, wherein said biodegradable and/or bioabsorbable polymer comprises a monomer selected from the group consisting of a glycolide, lactide, dioxanone, caprolactone, trimethylene carbonate, ethylene glycol and lysine.

10. A system according to claim 8, wherein said biodegradable and/or bioabsorbable polymer comprises a biodegradable and/or bioabsorbable linear aliphatic polyester.

11. A system according to claim 10, wherein said biodegradable and/or bioabsorbable linear aliphatic polyester is a polyglycolide or a copolymer poly(glycolide-co-lactide).

12. A system according to claim 1, wherein said biodegradable and/or bioabsorbable fiberizable material comprises a material derived from biological tissue.

13. A system according to claim 1, wherein said fibers have diameters in the range from about 10 up to 1,000 nanometers.

14. A system according to claim 13, wherein said fibers have diameters in the range from about 20 to about 500 nanometers.

15. A system according to claim 1, further comprising small blobs of biodegradable and/or bioabsorbable material.

16. A system according to claim 1, further comprising at least one medicinal agent.

17. A system according to claim 16, wherein said medicinal agent is contained within said fibers.

18. A system according to claim 17, further comprising fibers with different concentrations of said medicinal agent.

19. A system according to claim 17, further comprising fibers with different medicinal agents.

20. A system according to claim 1, further comprising a plurality of layers, wherein at least one of the layers comprises a composite or asymmetric composite of different biodegradable and/or bioabsorbable fibers.

21. A system according to claim 20, further comprising at least one medicinal agent between at least two of said layers.

22. A system according to claim 1, wherein said fibrous article has a controlled degradation rate.

23. A system according to claim 1, wherein said fibrous article is a membrane.

24. A system according to claim 23, wherein said membrane has a thickness in the range of about 10 to about 5000 microns.

25. A system according to claim 24, wherein said membrane has a thickness in the range of about 20 to about 1000 microns.

26. A method for controlled delivery of a medicinal agent which comprises implanting at a target site in an animal, a system for controlled delivery of a medicinal agent, said system comprising a medicinal agent to be delivered and a biodegradable and/or bioabsorbable fibrous article physically associated with said medicinal agent to release said agent at a controlled rate, wherein said article comprises a composite of different biodegradable and/or bioabsorbable fibers or an asymmetric composite of different biodegradable and/or bioabsorbable fibers.

27. A method according to claim 26, wherein different fibers refers to fibers of different diameters.

28. A method according to claim 26, wherein different fibers refers to fibers of different biodegradable and/or bioabsorbable materials.

29. A method according to claim 26, wherein different fibers refers to fibers of different diameters and different biodegradable and/or bioabsorbable materials.

* * * * *

UNITED STATES PATENT AND TRADEMARK OFFICE
CERTIFICATE OF CORRECTION

PATENT NO.    : 6,689,374 B2
DATED         : February 10, 2004
INVENTOR(S)   : Chu et al.

It is certified that error appears in the above-identified patent and that said Letters Patent is hereby corrected as shown below:

Column 1,
Line 5, after the title, insert -- This invention was made with government support under Grant Nos. DMR 9984102 and DMR 9732653 awarded by the National Science Foundation. The Government has certain rights in the invention. --

Signed and Sealed this

Twenty-fifth Day of May, 2004

JON W. DUDAS
*Acting Director of the United States Patent and Trademark Office*